(12) United States Patent
Labelle et al.

(10) Patent No.: US 6,436,965 B1
(45) Date of Patent: Aug. 20, 2002

(54) PDE IV INHIBITING AMIDES, COMPOSITIONS AND METHODS OF TREATMENT

(75) Inventors: Marc Labelle, Burlingame, CA (US); Claudio Sturino, Dorval (CA); Nicolas Lachance, Pierrefonds (CA); Dwight Macdonald, L'ile Bizard (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/797,083

(22) Filed: Mar. 1, 2001

Related U.S. Application Data
(60) Provisional application No. 60/186,571, filed on Mar. 2, 2002.

(51) Int. Cl.[7] ............... A61K 31/4439; C07D 401/12
(52) U.S. Cl. ............... 514/339; 546/277.7; 546/269.4; 546/256; 546/113; 548/251; 548/484; 514/300; 514/333; 514/381; 514/418
(58) Field of Search ................ 514/339, 333, 514/300, 381, 418; 546/277.7, 256, 268.4, 113; 548/251, 484

(56) References Cited

U.S. PATENT DOCUMENTS

| | | |
|---|---|---|
| 4,675,332 A | 6/1987 | Connor et al. |
| 4,761,424 A | 8/1988 | Carethers et al. |
| 4,868,200 A | 9/1989 | Carethers et al. |
| 6,251,923 B1 | 6/2001 | Hofgen et al. |

FOREIGN PATENT DOCUMENTS

EP  0 186 367  7/1986

OTHER PUBLICATIONS

Unangst, P.C. et al. : Novel Indolecarboxamidotetrazoles as potential antiallery agents. J. Med. Chem. 1989, vol. 32, pp. 1360–1366.*

* cited by examiner

*Primary Examiner*—Charanjit S. Aulakh
(74) *Attorney, Agent, or Firm*—Raynard Yuro; David L. Rose

(57) ABSTRACT

Compounds represented by formula I:

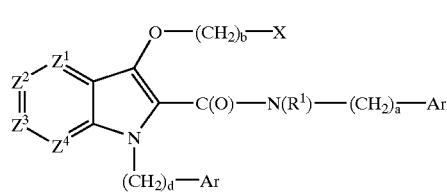

as well as pharmaceutically acceptable salts and hydrates thereof are disclosed as useful for treating or preventing diseases and conditions mediated by PDE-IV.

Pharmaceutical compositions and methods of treatment are also included.

17 Claims, No Drawings

PDE IV INHIBITING AMIDES, COMPOSITIONS AND METHODS OF TREATMENT

CROSS-REFERENCE TO RELATED APPLICATIONS

This application claims the benefit of U.S. Provisional Application No. 60/186,571 filed on Mar. 2, 2000.

BACKGROUND OF THE INVENTION

This invention relates to compounds and pharmaceutical compositions for the treatment of diseases by raising the level of cyclic adenosine-3',5'-monophosphate (cAMP) through the inhibition of phosphodiesterase IV (PDE IV).

Many hormones and neurotransmitters modulate tissue function by elevating intracellular levels of 3',5'-cyclic adenosine monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). At least seven members of the family have been described (PDE I–VII), the distribution of which varies from tissue to tissue. This suggests that specific inhibitors of PDE isoenzymes could achieve differential elevation of cAMP in different tissues [for reviews of PDE distribution, structure, function and regulation, see Beavo & Reifsnyder (1990) TIPS, 11: 150–155, Nicholson et. al. (1991) TIPS, 12: 19–27, and Torphy and Undem (1991) Thorax, 46: 512–523].

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) J. Immunol., 148: 2503–2510) and eosinophils (Dent G. et al., (1991) Br. J. Pharmacol., 103: 1339–1346) and that inhibition of this isotype is associated with the inhibition of cell activation. Furthermore, elevation of cAMP in airway smooth muscle has a spasmolytic effect. Consequently PDE IV inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. PDE IV has been shown to exist in four isoforms (A, B, C and D) to date, each coded for by a separate gene in both rodents (Swinnen J. V. et al., (1989) Proc. Natl. Acad. Sci. USA, 86: 5325–5329) and man (Bolger G. et al., (1993) Mol. Cell Biol., 13: 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al., 1989; Bolger et al., 1993; Obernolte R. et al., (1993) Gene, 129: 239–247, ibid) and the high degree of sequence conservation amongst isoforms of different species.

To date, full length cDNAs for human PDE IVA, B and D (Bolger et al., 1993 ibid; Obernolte et al., 1993 ibid; Mclaughlin M. et al., (1993) J. Biol. Chem., 268: 6470–6476) and rat PDE IVA, B and D (Davis R. et al., (1989) Proc. Natl. Acad. Sci. USA, 86: 3604–3608; Swinnen J. V. et al., (1991) J. Biol. Chem., 266: 18370–18377), have been reported, enabling functional recombinant enzymes to be produced by expression of the cDNAs in an appropriate host cell. These cDNAs have been isolated by conventional hybridization methods. However using this approach, only partial cDNAs for both human and rat PDE IVC have been obtained. (Bolger et al., ibid. 1993 and Swinnen et al., ibid. 1989 and International Patent Specification No. WO 91/16457.)

The design of PDE IV inhibitors for the treatment of inflammatory diseases such as asthma, has met with limited success to date. Many of the PDE IV inhibitors which have been synthesised have lacked potency and/or inhibit more than one type of PDE isoenzyme in a non-selective manner. PDE IV inhibitors that are relatively potent and selective for PDE IV, are reported to be emetic as well. Indeed this side effect has been so universal that experts have expressed their belief that the emesis experienced upon administration of a PDE IV inhibitor may be mechanism based.

The compounds described herein are potent inhibitors of PDE IV at concentrations that exhibit little or no inhibitory action on other PDE isoenzymes. These compounds inhibit the human recombinant PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. Advantageously, compounds according to the invention have good oral activity, and at orally effective doses exhibit little or none of the side-effects associated with known PDE IV inhibitors, such as rolipram. The compounds of the invention are therefore of use in medicine, especially in the prophylaxis and treatment of asthma and other inflammatory conditions.

SUMMARY OF THE INVENTION

A compound represented by formula I:

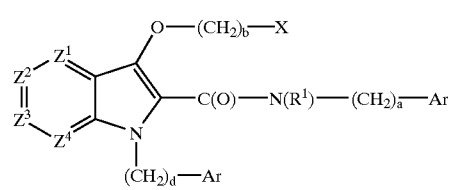

or a pharmaceutically acceptable salt or hydrate thereof wherein:
one of $Z^1$, $Z^2$, $Z^3$ and $Z^4$ represents N or $CR^2$ and the others represent $CR^2$;
a represents 0 or 1;
b represents 0, 1 or 2;
d represents 0, 1 or 2;
$R^1$ represents H, $C_{1-4}$alkyl or hydroxy$C_{1-4}$alkyl;
each $R^2$ is independently selected from the group consisting of:
H, halo, $C_{1-8}$alkyl, halo$C_{1-8}$alkyl, hydroxy$C_{1-8}$alkyl, CN, Het, $OR^a$, $OC(O)N(R^b)_2$, $NR^bC(O)R^a$, $C(R^a)_2CO_2R^a$, $C_{1-8}$alkyl$N(R^b)_2$, halo$C_{1-8}$alkyl$N(R^b)_2$, $CO_2R^a$, $C(O)N(R^b)_2$, $SO_2N(R^b)_2$, $S(O)_bR^d$ and $NR^bSO_2R^d$;
each $R^a$ is independently selected from H, $C_{1-4}$alkyl, $C_{1-4}$alkylNH$C_{1-4}$alkyl, and $C_{1-4}$alkylN($C_{1-4}$alkyl)$_2$, the alkyl portions of which are optionally substituted with 1–3 halo groups;

each $R^b$ is selected from H and C1–7alkyl, and when two $R^b$'s are present, they can be taken together and represent a fused ring system having 5–10 members, said ring system being saturated or containing 1–4 double bonds, and optionally including 1–3 heteroatoms selected from O, S and $NR^e$;

$R^d$ and $R^e$ are independently selected from Het, $C_{1-7}$alkyl, $C_{2-7}$alkenyl, $C_{2-7}$alkynyl, and $C_{1-7}$alkyl-Het;

Het represents a 5–10 membered aromatic, partially aromatic or non-aromatic ring system containing 1–4 heteroatoms selected from O, S and N, optionally substituted on any available position with oxo, $C_{1-4}$alkyl, halo, amino, hydroxy$C_{1-4}$ alkyl, halo$C_{1-4}$alkyl and amino$C_{1-4}$alkyl;

X represents $C_{3-7}$cycloalkyl or Ar;

and each Ar is independently selected from the group consisting of: phenyl, thienyl, thiazolyl, pyridyl, oxazolyl, tetrazolyl, pyrimidinyl, pyrazinyl and pyridazinyl, said Ar being optionally substituted with 1–4 members selected from: halo, hydroxy, CN, $C_{1-4}$alkyl, $C_{1-6}$haloalkyl, $C_{1-6}$hydroxyalkyl, $OC_{1-6}$alkyl, $OC_{1-6}$haloalkyl, $OC_{1-6}$hydroxyalkyl, $C_{1-6}$alkyl $OC_{1-6}$alkyl, $C_{1-6}$alkyl$OC_{1-6}$haloalkyl, $C(O)NH_2$, $C(O)NHC_{1-6}$alkyl, $C(O)N(C_{1-6}$alkyl$)_2$, $C_{1-6}$alkyl$OC_{1-6}$alkyl$C(O)NH_2$, $CO_2H$, $CO_2C_{1-6}$alkyl, $NHC(O)C_{1-6}$alkyl, $NHC(O)OC_{1-6}$alkyl, and $SO_2C_{1-6}$alkyl.

Pharmaceutical compositions and methods of treatment are also included.

DETAILED DESCRIPTION OF THE INVENTION

The invention encompasses compounds represented by formula I:

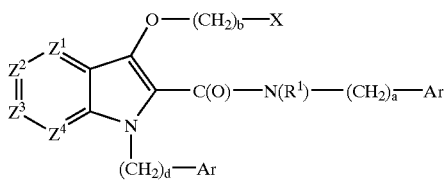

as well as pharmaceutically acceptable salts and hydrates thereof wherein:

one of $Z^1$, $Z^2$, $Z^3$ and $Z^4$ represents N or $CR^2$ and the others represent $CR^2$;

a represents 0 or 1;

b represents 0, 1 or 2;

d represents 0, 1 or 2;

$R^1$ represents H, $C_{1-4}$alkyl or hydroxy$C_{1-4}$alkyl;

each $R^2$ is independently selected from the group consisting of:

H, halo, $C_{1-8}$alkyl, halo$C_{1-8}$alkyl, hydroxy$C_{1-8}$alkyl, CN, Het, $OR^a$, $OC(O)N(R^b)_2$, $NR^bC(O)R^a$, $C(R^a)_2CO_2R^a$, $C_{1-8}$alkyl$N(R^b)_2$, halo$C_{1-8}$alkyl$N(R^b)_2$, $CO_2R^a$, $C(O)N(R^b)_2$, $SO_2N(R^b)_2$, $S(O)_bR^d$ and $NR^bSO_2R^d$;

each $R^a$ is independently selected from H, $C_{1-4}$alkyl, $C_{1-4}$alkyl$NHC_{1-4}$alkyl, and $C_{1-4}$alkyl$N(C_{1-4}$alkyl$)_2$, the alkyl portions of which are optionally substituted with 1–3 halo groups;

each $R^b$ is selected from H and C1–7alkyl, and when two $R^b$'s are present, they can be taken together and represent a fused ring system having 5–10 members, said ring system being saturated or containing 1–4 double bonds, and optionally including 1–3 heteroatoms selected from O, S and $NR^e$;

$R^d$ and $R^e$ are independently selected from Het, $C_{1-7}$alkyl, $C_{2-7}$alkenyl, $C_{2-7}$alkynyl, and $C_{1-7}$alkyl-Het;

Het represents a 5–10 membered aromatic, partially aromatic or non-aromatic ring system containing 1–4 heteroatoms selected from O, S and N, optionally substituted on any available position with oxo, $C_{1-4}$alkyl, halo, amino, hydroxy$C_{1-4}$ alkyl, halo$C_{1-4}$alkyl and amino$C_{1-4}$alkyl;

X represents $C_{3-7}$cycloalkyl or Ar;

and each Ar is independently selected from the group consisting of: phenyl, thienyl, thiazolyl, pyridyl, oxazolyl, tetrazolyl, pyrimidinyl, pyrazinyl and pyridazinyl, said Ar being optionally substituted with 1–4 members selected from: halo, hydroxy, CN, $C_{1-4}$alkyl, $C_{1-6}$haloalkyl, $C_{1-6}$hydroxyalkyl, $OC_{1-6}$alkyl, $OC_{1-6}$haloalkyl, $OC_{1-6}$hydroxyalkyl, $C_{1-6}$alkyl $OC_{1-6}$alkyl, $C_{1-6}$alkyl$OC_{1-6}$haloalkyl, $C(O)NH_2$, $C(O)NHC_{1-6}$alkyl, $C(O)N(C_{1-6}$alkyl$)_2$, $C_{1-6}$alkyl $OC_{1-6}$alkyl$C(O)NH_2$, $CO_2H$, $CO_2C_{1-6}$alkyl, $NHC(O)C_{1-6}$alkyl, $NHC(O)OC_{1-6}$alkyl, and $SO_2C_{1-6}$alkyl.

As used herein, the following terms and definitions apply.

Alkyl includes straight, branched and cyclic groups containing the indicated number of carbon atoms. If no number is specified, $C_{1-6}$alkyl is appropriate.

Alkenyl refers to a carbon containing group having from 2–7 carbon atoms unless otherwise indicated, and 1–3 carbon-carbon double bonds. It can be straight, branched or cyclic as appropriate.

Alkynyl refers to a carbon containing group having from 2–7 carbon atoms, and 1–3 carbon-carbon triple bonds. It can be straight, branched or cyclic.

Halo includes F, I, Br and Cl. When haloalkyl is indicated, this includes monohalogenated alkyl groups containing the indicated number of carbon atoms, dihalo, trihalo, etc. up to perhaloalkyl groups.

Het represents a 5–10 membered aromatic, partially aromatic or non-aromatic ring system containing 1–4 heteroatoms selected from O, S and N, optionally substituted on any available position with oxo, $C_{1-4}$alkyl, halo, amino, hydroxy$C_{1-4}$ alkyl, halo$C_{1-4}$alkyl and amino$C_{1-4}$alkyl. Thus, examples of Het include well known heteroaryl rings, such as pyridine, pyrrole, pyrimidine, imidazole, triazole, tetrazole, and the like, as well as non-aromatic rings, such as piperidine, pyrrolidine and the like.

Ar is an aromatic ring and is selected from the group consisting of: phenyl, thienyl, thiazolyl, pyridyl, oxazolyl, tetrazolyl, pyrimidinyl, pyrazinyl and pyridazinyl. The Ar moiety is optionally substituted with 1–4 members selected from: halo, hydroxy, CN, $C_{1-4}$alkyl, $C_{1-6}$haloalkyl, $C_{1-6}$hydroxyalkyl, $OC_{1-6}$alkyl, $OC_{1-6}$haloalkyl, $OC_{1-6}$hydroxyalkyl, $C_{1-6}$alkyl$OC_{1-6}$alkyl, $C_{1-6}$alkyl $OC_{1-6}$haloalkyl, CN, $C(O)NH_2$, $C(O)NHC_{1-6}$alkyl, $C(O)N(C_{1-6}$alkyl)2, $C_{1-6}$alkyl$OC_{1-6}$alkyl$C(O)NH_2$, $CO_2H$, $CO_2C_{1-6}$alkyl, $NHC(O)C_{1-6}$alkyl, $C_{1-6}$alkyl$OC(O)NH$ and $SO_2C_{1-6}$alkyl.

The following abbreviations have the indicated meanings:

Ac=acetyl

Bn=benzyl cAMP=cyclic adenosine-3',5'-monophosphate
DBU=1,8-diazabicyclo[5.4.0]undec-7-ene
DIBAL diisobutylaluminum hydride
DMAP=4-(dimethylamino)pyridine
DMF=N,N-dimethylformamide
$Et_3N$=triethylamine
GST=glutathione transferase
LDA=lithium diisopropylamide
m-CPBA=metachloroperbenzoic acid
MMPP=monoperoxyphthalic acid
MPPM=monoperoxyphthalic acid, magnesium salt $6H_2O$
Ms=methanesulfonyl=mesyl=$SO_2Me$
MsO=methanesulfonate=mesylate
NSAID=non-steroidal anti-inflammatory drug
o-Tol=ortho-tolyl
OXONE®=$2KHSO_5 \cdot KHSO_4 \cdot K_2SO_4$
PCC=pyridinium chlorochromate
PDC=pyridinium dichromate
PDE phosphodiesterase
Ph=phenyl
Phe=benzenediyl
PMB=para-methoxybenzyl
Pye=pyridinediyl
r.t.=room temperature
rac.=racemic
SAM=aminosulfonyl or sulfonamide or $SO_2NH_2$
SEM=2-(trimethylsilyl)ethoxymethoxy
SPA=scintillation proximity assay
TBAF=tetra-n-butylammonium fluoride
Th=2- or 3-thienyl
TFA=trifluoroacetic acid
TFAA=trifluoroacetic acid anhydride
THF=tetrahydrofuran
Thi=thiophenediyl
TLC=thin layer chromatography
TMS-$CF_3$=trimethyl(trifluoromethyl)silane
TMS-CN=trimethylsilyl cyanide
Tz=1H (or 2H)-tetrazol-5-yl
$C_3H_5$=allyl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl In one aspect of the invention that is of interest, all four of $Z^1$, $Z^2$, $Z^3$ and $Z^4$ represent $CR^2$. Within this aspect of the invention, all other variables are as originally defined.

In another aspect of the invention that is of interest, b represents 0 or 1. Within this aspect of the invention, all other variables are as originally defined.

In another aspect of the invention, d represents 1. Within this aspect of the invention, all other variables are as originally defined.

In another aspect of the invention, $R^1$ represents H or $CH_3$. Within this aspect of the invention, all other variables are as originally defined.

In another aspect of the invention, each $R^2$ is independently selected from the group consisting of H, $C_{1-8}$alkyl, hydroxy$C_{1-8}$alkyl, $CO_2R^a$, $C_{1-8}$alkylN$(R^b)_2$ and $C(O)N(R^b)_2$. $R^b$ is selected from H and $C_{1-3}$alkyl. Within this aspect of the invention, all other variables are as originally defined.

In another aspect of the invention, X represents Ar and Ar is independently selected from the group consisting of: phenyl, pyridyl and tetrazolyl,
said Ar being optionally substituted with 1–4 members selected from: halo, CN, $C_{1-4}$alkyl, $C_{1-6}$haloalkyl, $OC_{1-6}$alkyl, $OC_{1-6}$haloalkyl, $C_{1-6}$hydroxyalkyl, $C(O)NH_2$, $C(O)NHC_{1-6}$alkyl, $C(O)N(C_{1-6}$alkyl$)_2$, $CO_2H$, $CO_2C_{1-6}$alkyl, $NHC(O)C_{1-6}$alkyl, $NHC(O)OC_{1-6}$alkyl and $SO_2C_{1-6}$alkyl. Within this aspect of the invention, all other variables are as originally defined.

A subset of compounds that is of particular interest relates to compounds of formula I wherein:
$Z^1$, $Z^2$, $Z^3$ and $Z^4$ represent $CR^2$;
each $R^2$ is independently selected from the group consisting of H, $C_{1-8}$alkyl, hydroxy$C_{1-8}$alkyl, $CO_2R^a$, $C_{1-8}$alkylN$(R^b)_2$ and $C(O)N(R^b)_2$ wherein $R^b$ is selected from H and $C_{1-3}$alkyl;
b represents 0 or 1;
d represents 1;
$R^1$ represents H or $CH_3$;
X represents Ar and
Ar is independently selected from the group consisting of: phenyl, pyridyl and tetrazolyl, said Ar being optionally substituted with 1–4 members selected from: halo, CN, $C_{1-4}$alkyl, $C_{1-6}$haloalkyl, $OC_{1-6}$alkyl, $OC_{1-6}$haloalkyl, $C_{1-6}$hydroxyalkyl, $C(O)NH_2$, $C(O)NHC_{1-6}$alkyl, $C(O)N(C_{1-6}$alkyl$)_2$, $CO_2H$, $CO_2C_{1-6}$alkyl, $NHC(O)C_{1-6}$alkyl, $NHC(O)OC_{1-6}$alkyl and $SO_2C_{1-6}$alkyl. Within this aspect of the invention, all other variables are as originally defined.

A further subset of compounds of the invention that is of interest is represented by Formula Ia:

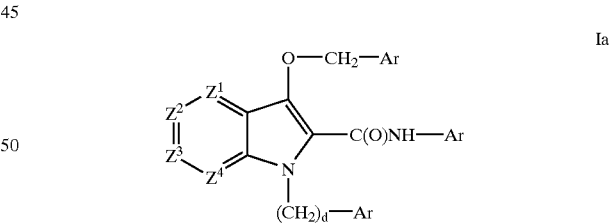

Ia

Within this subset, all variables are as originally defined.

More particularly, a subset of compounds that is of interest relates to compounds of formula Ia wherein $Z^1$, $Z^2$, $Z^3$ and $Z^4$ represent $CR^2$. Within this subset, all variables are as originally defined.

More particularly, a subset of compounds that is of interest relates to compounds of formula Ia wherein each $R^2$ is independently selected from the group consisting of H, $C_{1-8}$alkyl, hydroxy$C_{1-8}$alkyl, $CO_2R^a$, $C_{1-8}$alkylN$(R^b)_2$ and $C(O)N(R^b)_2$ wherein $R^a$ is independently selected from H and $C_{1-4}$alkyl, and $R^b$ is selected from H and $C_{1-3}$alkyl.

More particularly, a subset of compounds that is of interest relates to compounds of formula Ia wherein each Ar is selected from phenyl, pyridyl and tetrazolyl, optionally substituted with 1–4 members selected from: halo, CN, $C_{1-4}$alkyl, $C_{1-6}$haloalkyl, $OC_{1-6}$alkyl, $OC_{1-6}$haloalkyl, $C_{1-6}$hydroxyalkyl, $C(O)NH_2$, $C(O)NHC_{1-6}$alkyl, $C(O)N(C_{1-6}alkyl)_2$, $CO_2H$, $CO_2C_{1-6}$alkyl, $NHC(O)C_{1-6}$alkyl, $NHC(O)OC_{1-6}$alkyl and $SO_2C_{1-6}$alkyl. Within this aspect of the invention, all other variables are as originally defined.

Examples of compounds falling within the present invention include the following:

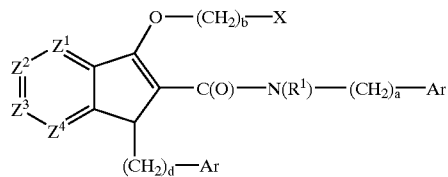

I

| Cpd | Z's | $(CH_2)_b$—(O)$_a$—$(CH_2)_b$—X | $N(R^1)(CH_2)_a$—Ar | $(CH_2)_d$—Ar |
|---|---|---|---|---|
| 1 | CH | OCH$_2$-Phe-4-F | N(Me)-3-Pyr | Bnzl |
| 2 | CH | OCH$_2$-Phe-4-F | N(Me)-4-Pyr | Bnzl |
| 3 | CH | OCH$_2$-Phe-4-F | N(Me)-Phe-3,4-di-OMe | Bnzl |
| 4 | CH | OCH$_2$-Phe-4-F | N(Me)-Phe-3,4-di-F | Bnzl |
| 5 | CH | OCH$_2$-Phe-4-F | N(Me)-5-Pyr-2-OMe | Bnzl |
| 6 | CH | OCH$_2$-Phe-4-F | N(Me)-5-tetrazolyl | Bnzl |
| 7 | CH | OCH$_2$-Phe-4-F | N(Me)-4-Pyr-2-OMe | Bnzl |
| 8 | CH | OCH$_2$-Phe-4-F | N(Me)-5-Pyr-2-CN | Bnzl |
| 9 | CH | OCH$_2$-Phe-4-F | N(Me)-4-Pyr-2-OMe | Bnzl |
| 10 | CH | O-Bnzl | NH-Phe-3,4-di-OMe | Bnzl-4-F |
| 11 | CH | O-Bnzl | NH-3-Pyr | Bnzl-4-F |
| 12 | CH | OCH$_2$-Phe-3-OCF$_2$H | NH-3-Pyr | Bnzl-3-OCF$_2$H |
| 13 | CH | OCH$_2$-Phe-3-OCF$_2$H | NH-4-Pyr | Bnzl-3-OCF$_2$H |
| 14 | CH | OCH$_2$-Phe-3-OCF$_2$H | NH-Phe-3,4-di-OMe | Bnzl-3-OCF$_2$H |
| 15 | CH | OCH$_2$-Phe-3-OCF$_2$H | NH-Phe-3,4-di-F | Bnzl-3-OCF$_2$H |
| 16 | CH | O-Bnzl | NH-3-Pyr | Bnzl-4-OCF$_2$H |
| 17 | CH | OCH$_2$-Phe-3-OMe | NH-3-Pyr | Bnzl-4-OCF$_2$H |
| 18 | CH | OCH$_2$-Phe-3-OMe | NH-5-tetrazolyl | Bnzl-4-OCF$_2$H |
| 19 | CH | OCH$_2$-Phe-3-OMe | NH-4-Pyr-2-OMe | Bnzl-4-OCF$_2$H |
| 20 | CH | OCH$_2$-Phe-3-OMe | NH-4-Pyr | Bnzl-4-OCF$_2$H |
| 21 | CH | OCH$_2$-Phe-3-OMe | NH-4-Pyr-2-NHC(O)Me | Bnzl-4-OCF$_2$H |
| 22 | CH | OCH$_2$-Phe-3-OMe | NH-3-Pyr | Bnzl-4-F |
| 23 | CH | OCH$_2$-Phe-3-OMe | NH-5-tetrazolyl | Bnzl-4-F |
| 24 | CH | OCH$_2$-Phe-3-OMe | NH-4-Pyr-2-OMe | Bnzl-4-F |
| 25 | CH | OCH$_2$-Phe-3-OMe | NH-4-Pyr | Bnzl-4-F |
| 26 | CH | OCH$_2$-Phe-3-OMe | NH-4-Pyr-2-NHC(O)Me | Bnzl-4-F |
| 27 | CH | OCH$_2$-Phe-3-OMe | NH-5-pyrimidinyl | Bnzl-4-F |
| 28 | CH | O-Bnzl | NH-3-Pyr | Bnzl-3,4-di-F |
| 29 | CH | O-Bnzl | NH-4-Pyr | Bnzl-3,4-di-F |
| 30 | CH | O-Bnzl | NH-Phe-3,4-di-OMe | Bnzl-3,4-di-F |
| 31 | CH | O-Bnzl | NH-Phe-3,4-di-F | Bnzl-3,4-di-F |
| 32 | CH | O-Bnzl | NH-5-Pyr-2-OMe | Bnzl-3,4-di-F |
| 33 | CH | O-Bnzl | NH-5-tetrazolyl | Bnzl-3,4-di-F |
| 34 | CH | O-Bnzl | NH-4-Pyr-2-OMe | Bnzl-3,4-di-F |

-continued $$\text{I}$$

Structure I: cyclopentene ring fused to aromatic ring with Z¹, Z², Z³, Z⁴; substituents O—(CH₂)ᵦ—X, C(O)—N(R¹)—(CH₂)ₐ—Ar, and (CH₂)ᵈ—Ar.

| Cpd | Z's | (CH₂)ᵦ—(O)ₐ—(CH₂)ᵦ—X | N(R¹)(CH₂)ₐ—Ar | (CH₂)ᵈ—Ar |
|---|---|---|---|---|
| 35 | CH | O-Bnzl | NH-5-Pyr-2-CN | Bnzl-3,4-di-F |
| 36 | CH | O-Bnzl | NH-5-Pyr-2-NHC(O)Me | Bnzl-3,4-di-F |
| 37 | CH | OCH₂-4-Pyr | NH-3-Pyr | Bnzl-4-CF₃ |
| 38 | CH | OCH₂-4-Pyr | NH-4-Pyr | Bnzl-4-CF₃ |
| 39 | CH | OCH₂-4-Pyr | NH-Phe-3,4-di-OMe | Bnzl-4-CF₃ |
| 40 | CH | OCH₂-4-Pyr | NH-Phe-3,4-di-F | Bnzl-4-CF₃ |
| 41 | CH | OCH₂-4-Pyr | NH-5-Pyr-2-OMe | Bnzl-4-CF₃ |
| 42 | CH | OCH₂-4-Pyr | NH-5-tetrazolyl | Bnzl-4-CF₃ |
| 43 | CH | OCH₂-4-Pyr | NH-4-Pyr-2-OMe | Bnzl-4-CF₃ |
| 44 | CH | OCH₂-4-Pyr | NH-5-Pyr-2-CN | Bnzl-4-CF₃ |
| 45 | CH | OCH₂-4-Pyr | NH-5-Pyr-2-NHC(O)Me | Bnzl-4-CF₃ |
| 46 | CH | OCH₂-4-Pyr | NH-3-Pyr | Bnzl |
| 47 | CH | OCH₂-4-Pyr | NH-4-Pyr | Bnzl |
| 48 | CH | OCH₂-4-Pyr | NH-Phe-3,4-di-OMe | Bnzl |
| 49 | CH | OCH₂-4-Pyr | NH-Phe-3,4-di-F | Bnzl |
| 50 | CH | OCH₂-4-Pyr | NH-5-Pyr-2-OMe | Bnzl |
| 51 | CH | OCH₂-4-Pyr | NH-5-tetrazolyl | Bnzl |
| 52 | CH | OCH₂-4-Pyr | NH-4-Pyr-2-OMe | Bnzl |
| 53 | CH | OCH₂-4-Pyr | NH-5-Pyr-2-CN | Bnzl |
| 54 | CH | OCH₂-4-Pyr | NH-5-Pyr-2-NHC(O)Me | Bnzl |
| 55 | CH | OCH₂-4-Pyr | NH-4-Pyr-2-NHC(O)OEt | Bnzl |
| 56 | CH | O-Bnzl | NH-3-Pyr | Bnzl |
| 57 | CH | O-Bnzl | NH-4-Pyr | Bnzl |
| 58 | CH | O-Bnzl | NH-Phe-3,4-di-OMe | Bnzl |
| 59 | $Z^1$ = N, all others = CH | O-Bnzl | NH-Phe-3,4-di-F | Bnzl |
| 60 | $Z^1$ = N, all others = CH | O-Bnzl | NH-5-Pyr-2-OMe | Bnzl |
| 61 | CH | O-Bnzl | NH-5-tetrazolyl | Bnzl |
| 62 | CH | O-Bnzl | NH-4-Pyr-2-OMe | Bnzl |
| 63 | CH | O-Bnzl | NH-5-Pyr-2-CN | Bnzl |
| 64 | CH | O-Bnzl | NH-5-Pyr-2-NHC(O)Me | Bnzl |
| 65 | CH | O-Bnzl | NH-4-Pyr-2-NHC(O)OEt | Bnzl |
| 66 | CH | OCH₂-4-Pyr | NH-3-Pyr | Bnzl-4-OCF₂H |
| 67 | CH | OCH₂-4-Pyr | NH-4-Pyr | Bnzl-4-OCF₂H |
| 68 | CH | OCH₂-4-Pyr | NH-Phe-3,4-di-OMe | Bnzl-4-OCF₂H |
| 69 | CH | OCH₂-4-Pyr | NH-Phe-3,4-di-F | Bnzl-4-OCF₂H |
| 70 | $Z^1$ = N, all others = CH | OCH₂-4-Pyr | NH-5-Pyr-2-OMe | Bnzl-4-OCF₂H |
| 71 | $Z^1$ = N, all others = CH | OCH₂-4-Pyr | NH-5-tetrazolyl | Bnzl-4-OCF₂H |
| 72 | $Z^1$ = N, all others = CH | OCH₂-4-Pyr | NH-4-Pyr-2-OMe | Bnzl-4-OCF₂H |
| 73 | CH | O-Bnzl | NH-3-Pyr | Bnzl-4-Me |
| 74 | CH | OCH₂-4-Pyr | NH-5-Pyr-2-CN | Bnzl-4-OCF₂H |
| 75 | CH | OCH₂-4-Pyr | NH-5-Pyr-2-NHC(O)Me | Bnzl-4-OCF₂H |
| 76 | $Z^4$ = CC(Me)₂OH all others = CH | OCH₂-4-Pyr | NH-5-tetrazolyl | Bnzl-4-CF₃ |

-continued $$I$$

Structure I: cyclopentene core with substituents: O—(CH$_2$)$_b$—X; Z$^1$, Z$^2$, Z$^3$, Z$^4$ on fused ring; C(O)—N(R$^1$)—(CH$_2$)$_a$—Ar; (CH$_2$)$_d$—Ar

| Cpd | Z's | (CH$_2$)$_b$—(O)$_a$—(CH$_2$)$_b$—X | N(R$^1$)(CH$_2$)$_a$—Ar | (CH$_2$)$_d$—Ar |
|---|---|---|---|---|
| 77 | Z$^4$ = CCO$_2$H<br>all others = CH | OCH$_2$-4-Pyr | NH-5-tetrazolyl | Bnzl-4-CF$_3$ |
| 78 | Z$^4$ = CCH$_2$NMe$_2$<br>all others = CH | OCH$_2$-4-Pyr | NH-5-tetrazolyl | Bnzl-4-CF$_3$ |
| 79 | Z$^4$ = CC(O)NMe$_2$<br>all others = CH | OCH$_2$-4-Pyr | NH-5-tetrazolyl | Bnzl-4-CF$_3$ |
| 80 | Z$^4$ = CBr<br>all others = CH | OCH$_2$-4-Pyr | NH-5-tetrazolyl | Bnzl-4-CF$_3$ |
| 81 | Z$^4$ = CSO$_2$NH$_2$<br>all others = CH | OCH$_2$-4-Pyr | NH-5-tetrazolyl | Bnzl-4-CF$_3$ |
| 82 | Z$^1$ = CC(Me)$_2$OH<br>all others = CH | OCH$_2$-4-Pyr | NH-5-tetrazolyl | Bnzl-4-CF$_3$ |
| 83 | Z$^1$ = CCO$_2$H<br>all others = CH | OCH$_2$-4-Pyr | NH-5-tetrazolyl | Bnzl-4-CF$_3$ |
| 84 | Z$^1$ = CCH$_2$NMe$_2$<br>all others = CH | OCH$_2$-4-Pyr | NH-5-tetrazolyl | Bnzl-4-CF$_3$ |
| 85 | Z$^1$ = CC(O)NMe$_2$<br>all others = CH | OCH$_2$-4-Pyr | NH-5-tetrazolyl | Bnzl-4-CF$_3$ |
| 86 | Z$^1$ = CBr<br>all others = CH | OCH$_2$-4-Pyr | NH-5-tetrazolyl | Bnzl-4-CF$_3$ |
| 87 | Z$^1$ = CSO$_2$NH$_2$<br>all others = CH | OCH$_2$-4-Pyr | NH-5-tetrazolyl | Bnzl-4-CF$_3$ |
| 88 | Z$^1$ = CC(Me)$_2$OH<br>all others = CH | OCH$_2$-4-Pyr | NH-4-Pyr | Bnzl-4-CF$_3$ |
| 89 | Z$^1$ = CCO$_2$H<br>all others = CH | OCH$_2$-4-Pyr | NH-4-Pyr | Bnzl-4-CF$_3$ |
| 90 | Z$^1$ = CCH$_2$NMe$_2$<br>all others = CH | OCH$_2$-4-Pyr | NH-4-Pyr | Bnzl-4-CF$_3$ |
| 91 | Z$^1$ = CC(O)NMe$_2$<br>all others = CH | OCH$_2$-4-Pyr | NH-4-Pyr | Bnzl-4-CF$_3$ |
| 92 | Z$^1$ = CBr<br>all others = CH | OCH$_2$-4-Pyr | NH-4-Pyr | Bnzl-4-CF$_3$ |
| 93 | Z$^1$ = CSO$_2$NH$_2$<br>all others = CH | OCH$_2$-4-Pyr | NH-4-Pyr | Bnzl-4-CF$_3$ |
| 94 | Z$^1$ = CC(Me)$_2$OH<br>all others = CH | O-Bnzl | NH-3-Pyr | Bnzl-4-F |
| 95 | Z$^1$ = CCO$_2$H<br>all others = CH | O-Bnzl | NH-3-Pyr | Bnzl-4-F |
| 96 | Z$^1$ = CCH$_2$NMe$_2$<br>all others = CH | O-Bnzl | NH-3-Pyr | Bnzl-4-F |
| 97 | Z$^1$ = CC(O)NMe$_2$<br>all others = CH | O-Bnzl | NH-3-Pyr | Bnzl-4-F |
| 98 | Z$^1$ = CBr<br>all others = CH | O-Bnzl | NH-3-Pyr | Bnzl-4-F |
| 99 | Z$^1$ = CSO$_2$NH$_2$<br>all others = CH | O-Bnzl | NH-3-Pyr | Bnzl-4-F |

-continued

![Structure I: cyclopentene ring fused with Z1-Z4 positions, bearing O-(CH2)b-X, C(O)-N(R1)-(CH2)a-Ar, and (CH2)d-Ar substituents]

I

| Cpd | Z's | (CH₂)ᵦ—(O)ₐ—(CH₂)ᵦ—X | N(R¹)(CH₂)ₐ—Ar | (CH₂)ᵈ—Ar |
|-----|-----|----------------------|----------------|-----------|
| 100 | Z⁴ = CC(Me)₂OH all others = CH | OCH₂-4-Pyr | NH-4-Pyr | Bnzl-4-CF₃ |
| 101 | Z⁴ = CCO₂H all others = CH | OCH₂-4-Pyr | NH-4-Pyr | Bnzl-4-CF₃ |
| 102 | Z⁴ = CCH₂NMe₂ all others = CH | OCH₂-4-Pyr | NH-4-Pyr | Bnzl-4-CF₃ |
| 103 | Z⁴ = CC(O)NMe₂ all others = CH | OCH₂-4-Pyr | NH-4-Pyr | Bnzl-4-CF₃ |
| 104 | Z⁴ = CBr all others = CH | OCH₂-4-Pyr | NH-4-Pyr | Bnzl-4-CF₃ |
| 105 | Z⁴ = CSO₂NH₂ all others = CH | OCH₂-4-Pyr | NH-4-Pyr | Bnzl-4-CF₃ |
| 106 | Z⁴ = CC(Me)₂OH all others = CH | O-Bnzl | NH-3-Pyr | Bnzl-4-F |
| 107 | Z⁴ = CCO₂H all others = CH | O-Bnzl | NH-3-Pyr | Bnzl-4-F |
| 108 | Z⁴ = CCH₂NMe₂ all others = CH | O-Bnzl | NH-3-Pyr | Bnzl-4-F |
| 109 | Z⁴ = CC(O)NMe₂ all others = CH | O-Bnzl | NH-3-Pyr | Bnzl-4-F |
| 110 | Z⁴ = CBr all others = CH | O-Bnzl | NH-3-Pyr | Bnzl-4-F |
| 111 | Z⁴ = CSO₂NH₂ all others = CH | O-Bnzl | NH-3-Pyr | Bnzl-4-F |
| 112 | Z³ = CC(Me)₂OH all others = CH | OCH₂-4-Pyr | NH-4-Pyr | Bnzl-4-CF₃ |
| 113 | Z³ = CCO₂H all others = CH | OCH₂-4-Pyr | NH-4-Pyr | Bnzl-4-CF₃ |
| 114 | Z³ = CCH₂NMe₂ all others = CH | OCH#-4-Pyr | NH-4-Pyr | Bnzl-4-CF₃ |
| 115 | Z³ = CC(O)NMe₂ all others = CH | OCH₂-4-Pyr | NH-4-Pyr | Bnzl-4-CF₃ |
| 116 | Z³ = CBr all others = CH | OCH₂-4-Pyr | NH-4-Pyr | Bnzl-4-CF₃ |
| 117 | Z³ = CSO₂NH₂ all others = CH | OCH₂-4-Pyr | NH-4-Pyr | Bnzl-4-CF₃ |
| 118 | Z³ = CC(Me)₂OH all others = CH | O-Bnzl | NH-3-Pyr | Bnzl-4-F |
| 119 | Z³ = CCO₂H all others = CH | O-Bnzl | NH-3-Pyr | Bnzl-4-F |
| 120 | Z³ = CCH₂NMe₂ all others = CH | O-Bnzl | NH-3-Pyr | Bnzl-4-F |
| 121 | Z³ = CC(O)NMe₂ all others = CH | O-Bnzl | NH-3-Pyr | Bnzl-4-F |
| 122 | Z³ = CBr all others = CH | O-Bnzl | NH-3-Pyr | Bnzl-4-F |

-continued $$\text{I}$$

Structure I: cyclopentene ring fused with Z¹,Z²,Z³,Z⁴ ring bearing O—(CH₂)ᵦ—X, C(O)—N(R¹)—(CH₂)ₐ—Ar, and (CH₂)_d—Ar substituents.

| Cpd | Z's | (CH₂)ᵦ—(O)ₐ—(CH₂)ᵦ—X | N(R¹)(CH₂)ₐ—Ar | (CH₂)_d—Ar |
|---|---|---|---|---|
| 123 | Z³ = CSO₂NH₂ all others = CH | O-Bnzl | NH-3-Pyr | Bnzl-4-F |
| 124 | Z² = CC(Me)₂OH all others = CH | OCH₂-4-Pyr | NH-4-Pyr | Bnzl-4-CF₃ |
| 125 | Z² = CCO₂H all others = CH | OCH₂-4-Pyr | NH-4-Pyr | Bnzl-4-CF₃ |
| 126 | Z² = CCH₂NMe₂ all others = CH | OCH₂-4-Pyr | NH-4-Pyr | Bnzl-4-CF₃ |
| 127 | Z² = CC(O)NMe₂ all others = CH | OCH₂-4-Pyr | NH-4-Pyr | Bnzl-4-CF₃ |
| 128 | Z² = CBr all others = CH | OCH₂-4-Pyr | N}I-4-Pyr | Bnzl-4-CF₃ |
| 129 | Z² = CSO₂NH₂ all others = CH | OCH₂-4-Pyr | NH-4-Pyr | Bnzl-4-CF₃ |
| 130 | Z² = CC(Me)₂OH all others = CH | O-Bnzl | NH-3-Pyr | Bnzl-4-F |
| 131 | Z² = CCO₂H all others = CH | O-Bnzl | NH-3-Pyr | Bnzl-4-F |
| 132 | Z² = CCH₂NMe₂ all others = CH | O-Bnzl | NH-3-Pyr | Bnzl-4-F |
| 133 | Z² = CC(O)NMe₂ all others = CH | O-Bnzl | NH-3-Pyr | Bnzl-4-F |
| 134 | Z² = CBr all others = CH | O-Bnzl | NH-3-Pyr | Bnzl-4-F |
| 135 | Z² = CSO₂NH₂ all others = CH | O-Bnzl | NH-3-Pyr | Bnzl-4-F |
| 136 | CH | O-Bnzl | NH-3-Pyr | Bnzl-4-C(Me)₂—OH |
| 137 | CH | OCH₂-3-Pyr | NH-3-Pyr | Bnzl-4-F |
| 138 | CH | OCH₂-3-Pyr | NH-4-Pyr | Bnzl-4-F |
| 139 | CH | OCH₂-3-Pyr | NH-Phe-3,4-di-OMe | Bnzl-4-F |
| 140 | CH | OCH₂-3-Pyr | NH-Phe-3,4-di-F | Bnzl-4-F |
| 141 | CH | OCH₂-3-Pyr | NH-5-Pyr-2-OMe | Bnzl-4-F |
| 142 | CH | O-Bnzl | NH-3-Pyr | Bnzl-4-CO₂Me |
| 143 | CH | OCH₂-3-Pyr | NH-5-tetrazolyl | Bnzl-4-F |
| 144 | CH | OCH₂-3-Pyr | NH-4-Pyr-2-OMe | Bnzl-4-F |
| 145 | CH | OCH₂-3-Pyr | NH-5-Pyr-2-CN | Bnzl-4-F |
| 146 | CH | OCH₂-3-Pyr | NH-5-Pyr-2-NHC(O)Me | Bnzl-4-F |
| 147 | CH | O-Bnzl | NH-Phe-3-SO₂Me | Bnzl-4-F |
| 148 | CH | O-Bnzl | NH-3-Pyr | Bnzl-4-CF₃ |
| 149 | CH | O—CH₂-cPr | NH-Phe-3,4-di-OMe | Bnzl-4-t-Bu |
| 150 | CH | O—CH₂-cPr | NH-5-tetrazolyl | Bnzl-4-t-Bu |
| 151 | CH | O—CH₂-cPr | NH-4-Pyr-2-OMe | Bnzl-4-t-Bu |
| 152 | CH | O—CH₂-cPr | NH-5-Pyr-2-OMe | Bnzl-4-t-Bu |
| 153 | CH | O—CH₂-cPr | NH-4-Pyr-2-NHC(O)OBt | Bnzl-4-t-Bu |
| 154 | CH | O—CH₂-cPr | NH-3-Pyr | Bnzl-4-F |
| 155 | CH | O—CH₂-cPr | NH-4-Pyr | Bnzl-4-F |
| 156 | CH | O—CH₂-cPr | NH-Phe-3,4-di-OMe | Bnzl-4-F |
| 157 | CH | O—CH₂-cPr | NH-Phe-3,4-di-F | Bnzl-4-F |

-continued

I

| Cpd | Z's | (CH₂)ᵦ—(O)ₐ—(CH₂)ᵦ—X | N(R¹)(CH₂)ₐ—Ar | (CH₂)ᵈ—Ar |
|---|---|---|---|---|
| 158 | CH | O—CH₂-cPr | NH-5-Pyr-2-OMe | Bnzl-4-F |
| 159 | CH | O—CH₂-cPr | NH-5-tetrazolyl | Bnzl-4-F |
| 160 | CH | O—CH₂-cPr | NH-4-Pyr-2-OMe | Bnzl-4-F |
| 161 | CH | O—CH₂-cPr | NH-5-Pyr-2-NHC(O)Me | Bnzl-4-F |
| 162 | CH | OCH₂-4-Pyr | NH-3-Pyr | Bnzl-4-F |
| 163 | CH | OCH₂-4-Pyr | NH-4-Pyr | Bnzl-4-F |
| 164 | CH | OCH₂-4-Pyr | NH-Phe-3,4-di-OMe | Bnzl-4-F |
| 165 | CH | OCH₂-4-Pyr | NH-Phe-3,4-di-F | Bnzl-4-F |
| 166 | CH | OCH₂-4-Pyr | NH-5-Pyr-2-OMe | Bnzl-4-F |
| 167 | CH | OCH₂-4-Pyr | NH-5-tetrazolyl | Bnzl-4-F |
| 168 | CH | OCH₂-4-Pyr | NH-4-Pyr-2-OMe | Bnzl-4-F |
| 169 | CH | OCH₂-4-Pyr | NH-5-Pyr-2-CN | Bnzl-4-F |
| 170 | CH | OCH₂-4-Pyr | NH-5-Pyr-2-NHC(O)Me | Bnzl-4-F |
| 171 | CH | OCH₂-4-Pyr | NH-4-Pyr-2-NHC(O)OEt | Bnzl-4-F |
| 172 | CH | O-Bnzl | NH-3-Pyr | Bnzl-4-t-Bu |
| 173 | CH | O-Bnzl | NH-3-Pyr | Bnzl-4-F |
| 174 | CH | O-Bnzl | NH-4-Pyr | Bnzl-4-F |
| 175 | CH | O-Bnzl | NH-Phe-3,4-di-OMe | Bnzl-4-F |
| 176 | CH | O-Bnzl | NH-Phe-3,4-di-F | Bnzl-4-F |
| 177 | CH | O-Bnzl | NH-5-Pyr-2-OMe | Bnzl-4-F |
| 178 | CH | O-Bnzl | NH-5-tetrazolyl | Bnzl-4-F |
| 179 | CH | O-Bnzl | NH-4-Pyr-2-OMe | Bnzl-4-F |
| 180 | CH | O-Bnzl | NH-5-Pyr-2-CN | Bnzl-4-F |
| 181 | CH | O-Bnzl | NH-5-Pyr-2-NHC(O)Me | Bnzl-4-F |
| 182 | CH | O-Bnzl | NH-4-Pyr-2-NHC(O)OEt | Bnzl-4-F |
| 183 | CH | O-Bnzl | N(Me)-3-Pyr | Bnzl-4-F |
| 184 | CH | O-Bnzl | N(Me)-3-Pyr | Bnzl-4-CF₃ |
| 185 | CH | O-Bnzl | 3-pyridylmethyl | Bnzl-4-F |
| 186 | CH | O-Bnzl | 4-pyridylmethyl | Bnzl-4-F |

Phe = phenyl, Bzyl = benzyl, Pyr = pyridyl

In another embodiment, the invention encompasses a pharmaceutical composition comprised of a compound of formula I in combination with a pharmaceutically acceptable carrier.

Within this embodiment, the invention encompasses pharmaceutical compositions for the treatment or prevention of diseases or conditions benefited by the inhibition of PDE IV, resulting in an elevation of cAMP, comprising a pharmaceutically acceptable carrier and a non-toxic therapeutically effective amount of compound of Formula I as described above.

The pharmaceutical compositions of the present invention comprise a compound of Formula I as an active ingredient or a pharmaceutically acceptable salt, thereof, and also contain a pharmaceutically acceptable carrier and optionally other therapeutic ingredients.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The compounds described herein contain one or more asymmetric centers and thus give rise to diastereomers and optical isomers. The present invention includes all such possible diastereomers as well as their racemic and resolved, enantiomerically pure forms and pharmaceutically acceptable salts thereof.

It will be understood that in the discussion of methods of treatment which follows, references to the compounds of Formula I is meant to include pharmaceutically acceptable salts.

Compounds according to the invention are selective and potent inhibitors of PDE IV. The ability of the compounds to act in this way may be determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, osteoporosis, chronic glomerulonephritis, atopic dermatitis, urticaria, adult and infant respiratory distress syndrome, diabetes, diabetes insipidus, allergic rhinitis, allergic conjunctivitis, vernal conjunctivitis, arterial restenosis and atherosclerosis.

Compounds of the invention also suppress neurogenic inflammation through elevation of cAMP in sensory neurons. They are, therefore, analgesic, antitussive and antihyperalgesic in inflammatory diseases associated with irritation and pain.

Compounds of the invention also elevate cAMP in lymphocytes and thereby suppress unwanted lymphocyte activation in immune-based diseases such as rheumatoid arthritis, ankylosing spondylitis, transplant rejection and graft versus host disease.

Compounds of the invention also reduce gastric acid secretion and therefore can be used to treat conditions associated with hypersecretion of gastric acid.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections, or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumor cells and can be used, therefore, to prevent tumor growth and invasion of normal tissues.

For the prevention, prophylaxis or treatment of disease, the compounds may be administered to a mammalian patient in need of such prevention, prophylaxis or treatment, in an amount that is effective for preventing, controlling or treating the disease. In addition to the treatment of warm-blooded animals such as mice, rats, horses, cattle sheep, dogs, cats, etc., the compounds of the invention are effective in the treatment of humans.

The compounds of Formula I may be administered orally, topically, parenterally, by inhalation spray or rectally in the form of a pharmaceutical composition as described herein.

The term parenteral as used herein includes subcutaneous, intravenous, intramuscular or intrasternal injection or infusion techniques.

The pharmaceutical composition containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known in the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Examples of such materials include cocoa butter and polyethylene glycols.

For topical use, creams, ointments, jellies, solutions or suspensions, etc., containing the compound of Formula I are employed. (For purposes of this application, topical application shall include mouth washes and gargles.)

Combined therapy to

The compounds of formula I can also be used in combination with another active ingredient or ingredients. For example, for the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxyephedrine; an antiitussive such as codeine, hydrocodone, caramiphen, carbetapentane, or dextramethorphan; a diuretic; and a sedating or non-sedating antihistamine such as loratidine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\beta$2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) (h) antagonists of the chemokine receptors, especially CCR-1, CCR-2, CCR-3, CXCR-3 and CCR-5; (i) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (j) anti-diabetic agents such as insulin, sulfonylureas, biguanides (metformin), α-glucosidase inhibitors (acarbose) and glitazones (troglitazone and pioglitazone); (k) preparations of interferon beta (interferon beta-1α, interferon beta-1β); (l) other compounds such as 5-aminosalicylic acid and prodrugs thereof, antimetabolites such as azathioprine and 6-mercaptopurine, and cytotoxic cancer chemotherapeutic agents.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration to humans may contain from about 0.5 mg to about 5 g of active agent compounded with an appropriate and convenient amount of carrier material which may vary from about 5 to about 95 percent of the total composition. Unit dosage forms will generally contain between from as low as about 1 mg to as high as about 1500 mg of an active ingredient, typically 25 mg, 50 mg, 100 mg, 200 mg, 300 mg, 400 mg, 500 mg, 600 mg, 800 mg or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of Formula I of the present invention can be prepared according to the synthetic routes outlined in Schemes I to IV and by following the methods described herein.

Scheme 1

Compounds of Formula I may be prepared by the method presented in Scheme 1 from an appropriately substituted anthranilic acid or Z=Nitrogen equivalent (II). Addition of an appropriate electrophile such as a $E^1Br$ or $E^1Cl$ (wherein $E^1$ represents $(CH_2)_d$—Ar in the presence of a base, followed by alkaline saponification of the ester group leads to III. Reaction of III with methyl bromoacetate, followed by esterification with diazomethane yields IV. Reaction with methoxide in methanol leads to the cyclization product V. Alkylation of the indanol with the appropriate electrophile such as $E^2Br$ (wherein $E^2$ represents $(CH_2)_b$—X in the presence of a base and in a suitable solvent such as DMF gives VI. Reaction of VI with an alkaline metal (such as Li, Mg or Al) derivative of the appropriate $NH_2$—$Ar^1$ in a suitable solvent such as THF yields VII. Alternatively, VI can be first saponified with conditions such as alcoholic NaOH, and then reacted with the $NH_2$—$Ar^1$ in the presence of an amide coupling reagent such as DCC in an appropriate solvent to give VII.

Following the same sequence of events but starting with an anthranitrile or its Z=N equivalent (VIII), one has access to the $X=CNR^4R^4$, $X=CNAr^1H$ and $X=CNR^4CH_2Ar^1$ series.

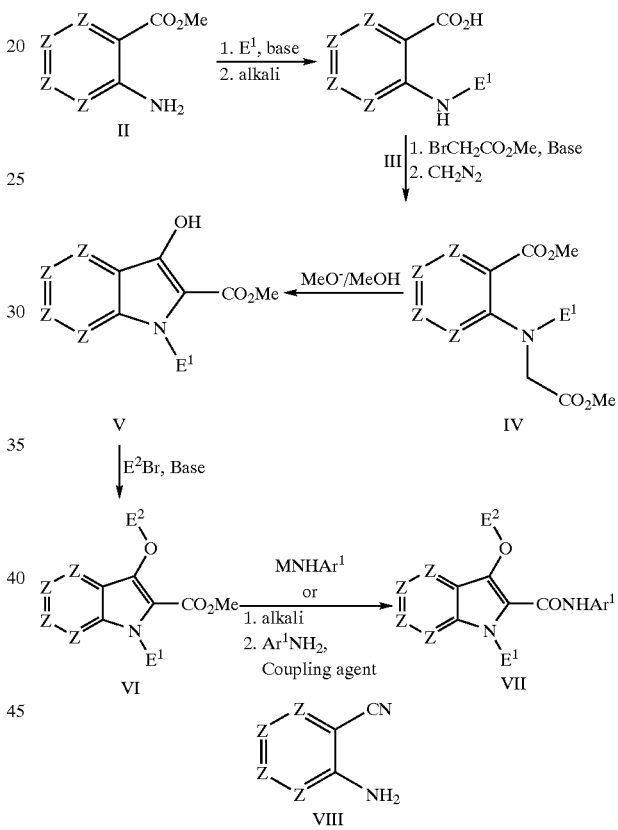

Scheme 2

Compounds of Formula I may alternatively be prepared by the method presented in Scheme 2 from an appropriately substituted indole or Z=Nitrogen equivalent (IX). Formylation in Vilsmeier-Haack or similar conditions gives X, which in turn can be oxidized under Baeyer-Villiger conditions to give XI. Successive reactions with electrophiles such as bromides, chlorides or iodides in the presence of bases and in a polar solvent gives XII, and then XIII. The ester group of XIII is transformed in the amide as described above in Scheme 1.

Alternatively, the reaction with the $E^1$ electrophile may be conducted on IX to give XV, and the $E^1$ group carried through the same sequence to give the same product XIV.

Scheme 2

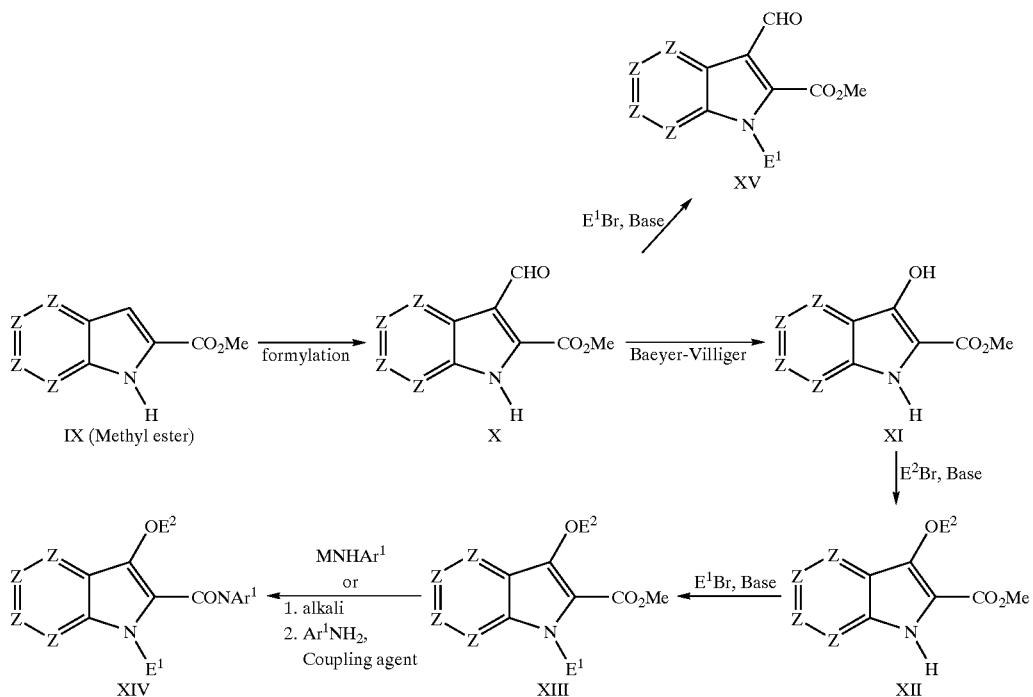

Scheme 3

Compounds of Formula I may alternatively be prepared by the method presented in Scheme 3 from an appropriately substituted indole or Z=Nitrogen equivalent (X). Grignard or other organometallic reagents may be added to X or to the XVI to yield the alcohol XVII, which in turn can be oxidized to the ketone XVIII. The rest of the sequence to compounds of Formula I is shown in Schemes 1 and 2.

In the case where W is H, with such reagents such as NaBH$_4$, the resulting primary alcohol may further be transformed by a Mitsunobu type reaction to give XIX, which can undergo the rest of the sequence to give compounds of Formula I.

Scheme 3

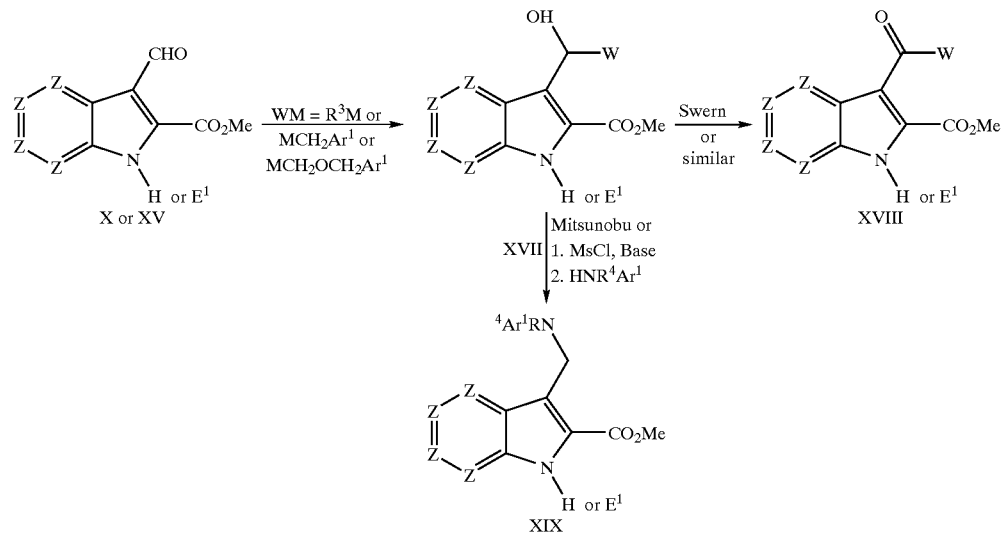

Scheme 4

Compounds of Formula IX may be prepared by the method presented in Scheme 4 from an appropriately substituted aldehyde (XX). Ethyl azidoacetate is condensed onto the aldehyde in a strong base such as ethoxide, and the resulting cinnamate is pyrolysed to yield the indole compound.

Scheme 4

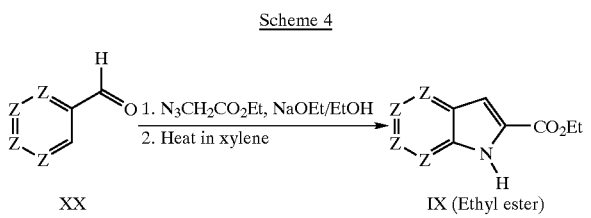

Scheme 5

Compounds of Formula IX may also be prepared by the method presented in Scheme 5 from an appropriately substituted methylated nitroaromatic (XXI). This compound is treated with a strong base such as ethoxide in ethanol, and condensed onto ethyl oxalate to give, after saponification, the pyruvic acid XXII. This acid is then esterified with diazomethane, for example, and then treated with a reagent such as iron in acetic acid to give the compound IX (Methyl ester).

Scheme 6

Compounds of formule I may be prepared by reaction of XIV first with a suitable metallation agent, such as n-BuLi, followed by trapping with an electrophile such as DMF to produce the aldehyde, acetone to produce the t-alcohol, $CO_2$ to produce the carboxylic acid.

and dissociated from the plate with PBS containing 0.5 mM EDTA. Cellular cAMP content was measured by centrifuging the cell suspension at 150 g×10 min. And resuspending the cells in a Hanks buffered salt solution at a density of $0.2×10^6$ cells/ml. The cells were preincubated at room temperature for 15 min. and then incubated with 10 µM prostaglandin $I_2$ ($PGI_2$) and the indicated compound for an additional 10 min. Basal cAMP levels were determined by incubating the cells in 0.1% DMSO. The incubations were terminated by the addition of HCl (0.1 N final) and the cells measured for cAMP as described below.

Determinations of whole-cell cAMP content were performed by incubating 100 µl reconstituted rabbit anti-succinyl cAMP serum with 100 µl of the whole-cell reaction or known cAMP standard and 30 pmol of $^{125}$I-cAMP TME in a ScintiStrip™ well (300 µl final volume) at room temperature for 18 h. Total cpm ($B_o$) was determined in the absence of sample of cAMP standard. The reaction mixture was then aspirated out of the well, and the individual wells were counted in a Beckman LS 6000SC with the window open from 10–999 for 1 min. The data were expressed as %B/$B_o$=[(standard or sample cpm−non-specific cpm)/($B_o$ cpm−non-specific cpm)]×100. Non-specific cpm were determined by incubating only the $^{125}$I-cAMP TME with assay buffer (50 mM acetate; pH 5.8) in the ScintiStrip™ well. All determinations were performed in triplicate.

Phosphodiesterase Scintillation Proximity Assay

CHO-K1 cells were lysed by sonication for 10 secs at a power setting of 50% (Braunsonic Model 2000) in an ice cold solution containing 50 mM Tris, pH 7.5; 1 mM EDTA; and 200 µM β-mercaptoethanol. The soluble and particulate fractions of the cell were obtained by centrifuging the sonicate for 90 min. at 100,000×g at 4° C. PDE activity was measured in a solution containing 50 mM Tris, pH 7.5; 10 mM $MgCl_2$; 1 mM EDTA; and 100 nM (or indicated) $^3$H-cAMP (100 µl final volume) in the presence of varying concentrations of inhibitor. The reaction mixture containing enzyme was incubated for 10 min. at 30° C. in 96-well View Plates (Packard), and terminated by the addition of 50 µl Phosphodiesterase Scintillation Proximity Assay (SPA) Beads (Amersham) containing 18 mM $ZnSO_4$. The amount of $^3$H-cAMP hydrolysis was determined by counting the plates in a Wallac 1450 µBeta LSC counter.

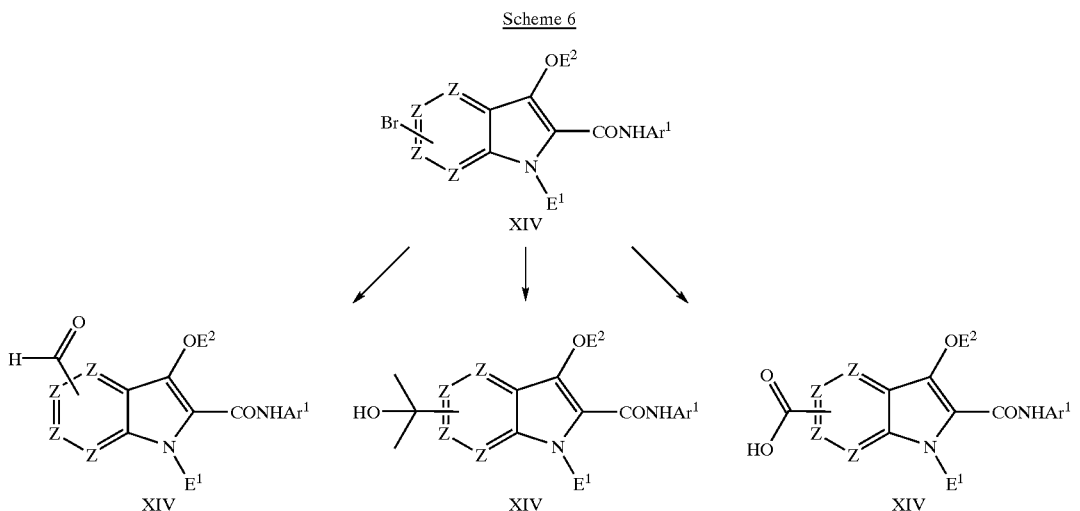

Assays for Determining Biological Activity

Measurement of Whole-cell cAMP Content

CHO-K1 cells were plated at a density of $10^6$ cells/175 $cm^2$ containing complete media with 500 µg/ml hygromycin. The flasks were maintained in an incubator at 37° C. with 5.0% $CO_2$ for 72 hr. The media was changed and the cells were allowed to grow overnight. The cells were washed The Elevation of cAMP in Leukocytes The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 $\mu$M.

Anti-alleraic Activity in Vivo

Compounds of the invention were tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar ravages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA Based PDE Activity Assay Protocol

Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 ul DMSO), 188 $\mu$l of substrate buffer containing [2,8-$^3$H] adenosine 3',5'-cyclic phosphate (cAMP, 100 nM to 50 $\mu$M), 10 mM $MgCl_2$, 1 mM EDTA, 50 mM Tris, pH 7.5. The reaction was initiated by the addition of 10 $\mu$l of human recombinant PDE-IV (the amount was controlled so that ~10% product was formed in 10 min. at 30° C). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit of the standard 4-parameter/multiple binding sites equation from a ten point titration.

LPS and fMLP-Induced TNF-a and $LTB_4$ Assays in Human Whole Blood

Whole blood provides a protein and cell-rich milieu appropriate for the study of biochemical efficacy of anti-inflammatory compounds such as PDE IV-selective inhibitors. Normal non-stimulated human blood does not contain detectable levels of TNF-$\alpha$ and $LTB_4$. Upon stimulation with LPS, activated monocytes expresss and secrete TNF-$\alpha$ up to 8 hours and plasma levels remain stable for 24 hours. Published studies have shown that inhibition of TNF-$\alpha$ by increasing intracellular cAMP via PDE IV inhibition and/or enhanced adenylyl cyclase activity occurs at the transcriptional level. $LTB_4$ synthesis is also sensitive to levels of intracellular cAMP and can be completely inhibited by PDE IV-selective inhibitors. As there is little $LTB_4$ produced during a 24 hour LPS stimulation of whole blood, an additional LPS stimulation followed by fP challenge of human whole blood is necessary for $LTB_4$ synthesis by activated neutrophils. Thus, using the same blood sample it is possible to evaluate the potency of a compound on two surrogate markers of PDE IV activity in the whole blood.

Fresh blood was collected in heparinized tubes by venipuncture from healthy human volunteers (male and female). These subjects had no apparent inflammatory conditions and had not taken any NSAIDs for at least 4 days prior to blood collection. Five hundred $\mu$L aliquots of blood were pre-incubated with either 2 $\mu$L of vehicle (DMSO) or 2 $\mu$L test compound at varying concentrations for 15 minutes at 37° C. This was followed by the addition of either 10 $\mu$L vehicle (PBS) as blanks or 10 $\mu$L LPS (1 $\mu$g/ml final concentration, Sigma Chem, #L-2630 from *E. coli*, serotype 0111:B4; diluted in 0.1% w/v BSA (in PBS)). After 24 hours of incubation at 37° C., another 10 $\mu$L of PBS (blank) or 10 $\mu$L of LPS (1 $\mu$g/ml final concentration) was added to blood and incubated for 30 minutes at 37° C. The blood was then challenged with either 10 $\mu$L of PBS (blank) or 10 $\mu$L of fMLP (1 $\mu$M final concentration, Sigma Chem #F-3506; diluted in 1% w/v BSA (in PBS)) for 15 minutes at 37° C. The blood samples were centrifuged at 1500×g for 10 minutes at 4° C. to obtain plasma. A 50 $\mu$L aliquot of plasma was mixed with 200 $\mu$L methanol for protein precipitation and centrifuged as above. The supernatant was assayed for $LTB_4$ using an enzyme immunoassay kit (Cayman Chemicals #520111) according to the manufacturer's procedure. TNF-$\alpha$ was assayed in diluted plasma (in PBS) using an ELISA kit (Cistron Biotechnology) according to manufacturer's procedure.

Assays for Determining Biological Activity

Measurement of Whole-cell cAMP Content

CHO-K1 cells were plated at a density of $10^6$ cells/175 $cm^2$ containing complete media with 500 $\mu$g/ml hygromycin. The flasks were maintained in an incubator at 37° C. with 5.0% $CO_2$ for 72 hr. The media was changed and the cells were allowed to grow overnight. The cells were washed and dissociated from the plate with PBS containing 0.5 mM EDTA. Cellular cAMP content was measured by centrifuging the cell suspension at 150 g×10 min. And resuspending the cells in a Hanks buffered salt solution at a density of 0.2×$10^6$ cells/ml. The cells were preincubated at room temperature for 15 min. and then incubated with 10 $\mu$M prostaglandin $I_2$ ($PGI_2$) and the indicated compound for an additional 10 min. Basal cAMP levels were determined by incubating the cells in 0.1% DMSO. The incubations were terminated by the addition of HCl (0.1 N final) and the cells measured for cAMP as described below.

Determinations of whole-cell cAMP content were performed by incubating 100 $\mu$l reconstituted rabbit anti-succinyl cAMP serum with 100 $\mu$l of the whole-cell reaction or known cAMP standard and 30 pmol of $^{125}$I-cAMP TME in a ScintiStrip™ well (300 $\mu$l final volume) at room temperature for 18 h. Total cpm ($B_o$) was determined in the absence of sample of cAMP standard. The reaction mixture was then aspirated out of the well, and the individual wells were counted in a Beckman LS 6000SC with the window open from 10–999 for 1 min. The data were expressed as %B/B$_o$=[(standard or sample cpm−non-specific cpm)/(B$_o$ cpm−non-specific cpm)]×100. Non-specific cpm were determined by incubating only the $^{125}$I-cAMP TME with assay buffer (50 mM acetate; pH 5.8) in the ScintiStrip™ well. All determinations were performed in triplicate.

Phosphodiesterase Scintillation Proximity Assay

CHO-K1 cells were lysed by sonication for 10 secs at a power setting of 50% (Braunsonic Model 2000) in an ice cold solution containing 50 mM Tris, pH 7.5; 1 mM EDTA; and 200 μM β-mercaptoethanol. The soluble and particulate fractions of the cell were obtained by centrifuging the sonicate for 90 min. at 100,000×g at 4° C. PDE activity was measured in a solution containing 50 mM Tris, pH 7.5; 10 mM MgCl$_2$; 1 mM EDTA; and 100 nM (or indicated) $^3$H-cAMP (100 μl final volume) in the presence of varying concentrations of inhibitor. The reaction mixture containing enzyme was incubated for 10 min. at 30° C. in 96-well View Plates (Packard), and terminated by the addition of 50 μl Phosphodiesterase Scintillation Proximity Assay (SPA) Beads (Amersham) containing 18 mM ZnSO$_4$. The amount of $^3$H-cAMT hydrolysis was determined by counting the plates in a Wallac 1450 μBeta LSC counter.

The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 M to 1 μM.

Anti-allergic Activity in Vivo

Compounds of the invention were tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001×10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA Based PDE Activity Assay Protocol

Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 ul DMSO), 188 μl of substrate buffer containing [2,8-$^3$H] adenosine 3',5'-cyclic phosphate (cAMP, 100 nM to 50 μM), 10 mM MgCl$_2$, 1 mM EDTA, 50 mM Tris, pH 7.5. The reaction was initiated by the addition of 10 μl of human recombinant PDE-IV (the amount was controlled so that ~10% product was formed in 10 min. at 30° C.). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. IC$_{50}$ value was approximated with a non-linear regression fit of the standard 4-parameter/multiple binding sites equation from a ten point titration.

LPS and fMLP-Induced TNF-a and LTB$_4$ Assays in Human Whole Blood

Whole blood provides a protein and cell-rich milieu appropriate for the study of biochemical efficacy of anti-inflammatory compounds such as PDE IV-selective inhibitors. Normal non-stimulated human blood does not contain detectable levels of TNF-α and LTB$_4$. Upon stimulation with LPS, activated monocytes expresss and secrete TNF-α up to 8 hours and plasma levels remain stable for 24 hours. Published studies have shown that inhibition of TNF-α by increasing intracellular cAMP via PDE IV inhibition and/or enhanced adenylyl cyclase activity occurs at the transcriptional level. LTB$_4$ synthesis is also sensitive to levels of intracellular cAMP and can be completely inhibited by PDE IV-selective inhibitors. As there is little LTB$_4$ produced during a 24 hour LPS stimulation of whole blood, an additional LPS stimulation followed by fMLP challenge of human whole blood is necessary for LTB$_4$ synthesis by activated neutrophils. Thus, using the same blood sample it is possible to evaluate the potency of a compound on two surrogate markers of PDE IV activity in the whole blood.

Fresh blood was collected in heparinized tubes by venipuncture from healthy human volunteers (male and female). These subjects had no apparent inflammatory conditions and had not taken any NSAIDs for at least 4 days prior to blood collection. Five hundred μL aliquots of blood were preincubated with either 2 μL of vehicle (DMSO) or 2 μL test compound at varying concentrations for 15 minutes at 37° C. This was followed by the addition of either 10 μL vehicle (PBS) as blanks or 10 μL LPS (1 μg/ml final concentration, Sigma Chem, #L-2630 from E. coli, serotype 0111:B4; diluted in 0.1% w/v BSA (in PBS)). After 24 hours of incubation at 37° C., another 10 μL of PBS (blank) or 10 μL of LPS (1 μg/ml final concentration) was added to blood and incubated for 30 minutes at 37° C. The blood was then challenged with either 10 μL of PBS (blank) or 10 μL of fMLP (1 μM final concentration, Sigma Chem #F-3506; diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for LTB$_4$ using an enzyme immunoassay kit (Cayman Chemicals #520111) according to the manufacturer's procedure. TNF-α was assayed in diluted plasma (in PBS) using an ELISA kit (Cistron Biotechnology) according to manufacturer's procedure.

EXAMPLES

The invention will now be illustrated in the following non-limiting Examples in which, unless otherwise stated:

1. All the end products of the formula I were analyzed by NMR, TLC and elementary analysis or mass spectroscopy.
2. Intermediates were analyzed by NMR and TLC.
3. Most compounds were purified by flash chromatography on silica gel, recrystallization and/or swish (suspension in a solvent followed by filtration of the solid).
4. The course of reactions was followed by thin layer chromatography (TLC) and reaction times are given for illustration only.

The following intermediates were prepared according to literature procedures, or purchased from the following vendor:
1. 4-Bromo-2-nitro-phenylpyruvic acid: Kosuge, T.; Ishida, H.; Inaba, A.; Nukaya, H. *Chem. Pharm. Bull.* 1985, 33, 1414–1419.
2. Ethyl 3-aminoindole-2-carboxylate: Unangst, P. C. *J. Heterocyclic Chem.* 1983, 20, 495–499.
3. Ethyl 5-bromoindole-2-carboxylate: BIOSYNTH AG.
4. Lithium 3-pyridylamide has been prepared such as lithium N-isopropylcyclohexylamide: Paquette, L. A.; Ewing, G. D. *J. Org. Chem.* 1975, 40, 2965–2966.

Example 1

{1-[(4-Fluorophenyl)methyl]-3-(phenylmethoxy)indol-2-yl}-N-(3-pyridyl)formamide (Compound 173)

Step 1: Methyl 2-{[(4-Fluorophenyl)methyl]amino}benzoate

A suspension of 77 g of potassium carbonate in a mixture of 100 mL of methyl ethyl ketone, 50 g of 4-fluorobenzyl bromide and 26 mL of the methyl 2-aminobenzoate was refluxed for 8 h, cooled to room temperature, filtered and concentrated. Filtration on 600 mL of silica gel and washing with 10% ethyl acetate in hexane afforded the desired material as a yellow oil (41 g, 85% purity). This material was used as such for the next step.

Step 2: Methyl 1-[(4-Fluorophenyl)methyl]-3-hydroxyindole-2-carboxylate

A solution of the previous ester (36 g) in 90 mL of MeOH, 27 mL of 10N aqueous NaOH and 225 mL of TBF was refluxed for 2 h. The reaction mixture was poured into 550 mL of 1N HCl and extracted three times with ethyl acetate. The organic phase was washed with brine and dried over MgSO$_4$. After evaporation, the solid was swished in 10% ether in hexane.

This solid was then combined with 28 mL of methyl bromoacetate and 37 g of K$_2$CO$_3$, in solution in 225 mL of MeOH and 450 mL H$_2$O. The mixture was refluxed for 18 h. The cooled reaction mixture was poured onto 65 mL of concentrated HCl in 700 mL of ice, and extracted with ethyl acetate. The organic extracts were dried over MgSO$_4$, titrated with an ether solution of CH$_2$N$_2$ and the solvents were evaporated under vacuum to give the crude diester.

This crude diester was dissolved in 450 mL of MeOH containing 20 g of sodium methoxide, and refluxed for 30 min. This mixture is then cooled and acidified with 2N HCl and extracted with ethyl acetate. The organic phase was dried over MgSO$_4$ and evaporated to dryness. The solid is swished in 200 mL of 5% ethyl acetate in hexane to give the title compound as a white solid.

$^1$H NMR (acetone-d$_6$) δ 3.91 (s, 3H), 5.69 (s, 2H), 7.04 (t, 2H), 7.10 (m, 3H), 7.37 (t, 1H), 7.51 (d, 1H), 7.72 (d, 1H), 8.7 (s, 1H).

Step 3: 1-[(4-Fluorophenyl)methyl]-3-(phenylmethoxy)indole-2-carboxylic Acid

To a solution 5.3 g of the previous ester and 2.53 mL of benzyl bromide in 17 mL of methyl ethyl ketone was added 3.18 g of K$_2$CO$_3$. The mixture was refluxed for 2 h and then cooled to room temperature. It was then filtered, the solids were washed with toluene and the combined liquid phases evaporated. Flash chromatography (toluene) yielded the methyl ester of the title compound as an orange solid. This ester was dissolved in 23 mL of ethanol and 5 mL water, and 2.3 mL of 10N NaOH was added. The mixture was heated for 40 min at 90° C. and then cooled. Acidification with 1N HCl and extraction with ethyl acetate yielded, after evaporation, an off-white solid.

$^1$H NMR (CDCl$_3$) δ 5.48 (s, 2H), 5.75 (s, 2H), 6.93 (t, 2H), 7.02 (t, 2H), 7.16 (m, 1H), 7.39 (m, 7H), 7.76 (d, 1H).

Step 4: {1-[(4-Fluorophenyl)methyl]-3-(phenylmethoxy)indol-2-yl}-N-(3-pyridyl)formamide Into a dry 25 mL round bottom flask was placed 1-[(4-fluorophenyl)methyl]-3-(phenylmethoxy)indole-2-carboxylic acid (50 mg) along with benzene (2.0 mL), i-Pr$_2$NEt (0.2 mL) followed by SOCl$_2$ (20 μL) and allowed to stir at room temperature for 0.5 hours. To the resulting mixture was then added 3-aminopyridine (20 mg) and stirred for an additional 4 hours. At this time, the reaction mixture was poured into a separatory funnel containing 25 mL H$_2$O/25 mL EtOAc, the layers were seperated and the aqueous layer was extracted with EtOAc (2×25 mL). The combined organic layers were dried over anhydrous MgSO$_4$, concentrated and the resulting material was purified by flash chromatography eluting with 50% EtOAc/hexanes to provide the title amide (14.1 mg) as a light yellow solid.

$^1$H NMR (CDCl$_3$) δ 5.45 (s, 2H), 5.90 (s, 2H), 6.92 (m, 2H), 7.08 (m, 2H), 7.20 (m, 2H), 7.40 (m, 7H), 7.82 (m, 1H), 8.02 (m, 1H), 8.04 (s, 1H), 8.28 (s, 1H), 9.55 (s, 1H). MS (+APCI) m/z 452.2 (M+H)$^+$.

Example 2

{1-[(4-Fluorophenyl)methyl]-3-(phenylmethoxy)indol-2-yl}-N-[3-(methylsulfonyl)phenyl]formamide (Compound 147)

Into a dry 50 mL round bottom flask was placed 1-[(4-fluorophenyl)methyl]-3-(phenylmethoxy)indole-2-carboxylic acid (50 mg) along with dry THF (5.0 mL), i-Pr$_2$NEt (0.1 mL), cooled to 0° C., added MsCl (10 μL) and allowed to stir for 0.5 hours. To this cold stirred solution 3-(methylsulfonyl)aniline (65 mg) was added and allowed to stir at room temperature for 2 hours. The resulting reaction mixture was poured into a separatory funnel containing 50 mL H$_2$O/50 mL EtOAc, the layers were separated, the aqueous layer was extracted with EtOAc (2×50 mL), the combined organic layers were washed with brine, dried over anhydrous MgSO$_4$ and concentrated. The resulting material was further purified by flash chromatography eluting with 50% EtOAc/hexanes to provide 42.4 mg of the title amide as an off-white solid.

$^1$H NMR (acetone-d$_6$) δ 3.10 (s, 2H), 5.59 (s, 2H), 5.96 (s, 2H), 7.00 (m, 2H), 7.17 (m, 3H), 7.43 (m, 4H), 7.56 (m, 6H), 7.98 (d, 1H), 8.27 (m, 1H), 9.82 (s, 1H).

Example 3

{1-[(4-Fluorophenyl)methyl]-3-(phenylmethoxy)indol-2-yl}-N-(3-pyridylmethyl)formamide (Compound 185)

Following the procedure describing the preparation of example 166, 1-[(4-fluorophenyl)methyl]-3-(phenylmethoxy)indole-2-carboxylic acid (50 mg) in THF (3.0 mL) at 0° C. was treated with i-Pr$_2$NEt (0.1 mL), MsCl (10 μL), stirred for 0.5 hours and then added 3-(aminomethyl)pyridine (20 mg). After work-up and purification by flash chromatography eluting with 30% EtOAc/hexanes the title amide (27.4 mg) was isolated as a light yellow oil.

$^1$H NMR (acetone-$d_6$) δ 4.52 (d, 2H), 5.37 (s, 2H), 6.97 (m, 2H), 7.07 (m, 3H), 7.30 (m, 7H), 7.58 (m, 1H), 7.61 (m, 1H), 7.82 (m, 1H), 8.18 (m, 1H) 8.46 (m, 1H), 8.54 (m, 1H). MS (+APCI) m/z 466.4 (M+H)$^+$.

Example 4

{1-[(4-Fluorophenyl)methyl]-3-(phenylmethoxy) indol-2-yl}-N-(4-pyridylmethyl)formamide (Compound 186)

Following the procedure describing the preparation of example 166, 1-[(4-fluorophenyl)methyl]-3-(phenylmethoxy)indole-2-carboxylic acid (50 mg) in THF (5.0 mL) at 0° C. was treated with i-Pr$_2$NEt (0.1 mL), MsCl (10 μL) and after 0.5 hours 4-aminomethylpyridine (20 mg) was added to the reaction mixture. After work-up and purification by flash chromatography eluting with 20% EtOAc/hexanes the title amide (15 mg) was obtained as a light yellow oil.

$^1$H NMR (acetone-$d_6$) δ 4.50 (m, 2H), 5.46 (s, 2H), 5.95 (s, 2H), 7.00 (m, 2H), 7.16 (m, 5H), 7.35 (m, 4H), 7.40 (m, 2H), 7.52 (m, 1H), 7.85 (m, 1H), 8.16 (m 1H), 8.46 (m, 2H).

Example 5

Methy 4-{[3-(Phenylmethoxy)-2-(N-(3-pyridyl) carbamoyl]methyl}benzoate (Compound 142)

Into a 100 mL round bottom flask was placed methyl 3-(phenylmethoxy)indole-2-carboxylate (1.0 g) along with THF (20 mL). To this stirred solution at room temperature was added lithium 3-pyridylamide (0.3 M in THF) until TLC indicated the consumption of starting material. The resulting reaction mixture was poured into a separatory funnel containing 50 mL H$_2$O/100 mL EtOAc, the layers were separated and the organic layer was washed with a 5% aqueous AcOH solution (2×50 mL). The organic layer was washed with brine, dried over anhydrous MgSO$_4$, concentrated and the residue was puridfied by flash chromatography eluting with 50% EtOAc/hexanes to provide 550 mg of the corresponding amide. To a flask containing the above amide (300 mg) in DMF (5.0 mL) at 0° C. was added 80 mg of a NaH suspension (60% in oil) and allowed to stir at room temperature for 0.5 hours. To this mixture was then added methyl 4-(bromomethyl)benzoate (225 mg) and the reaction was allowed to stir at room temperature overnight. At this time, the reaction mixture was poured into a separatory funnel containing 50 mL H$_2$O/50 mL EtOAc, the layers were separated and the aqueous layer was extracted with EtOAc (2×25 mL). The combined organic layers were washed with brine, dried over anhydrous MgSO$_4$, concentrated and purified by flash chromatography eluting with 30% EtOAc/hexanes. The title amide (175 mg) was obtained as an off-white solid.

$^1$H NMR (acetone-$d_6$) δ 3.82 (s, 3H), 5.62 (s, 2H), 6.06 (s, 2H), 7.23 (m, 4H), 7.36 (m, 4H), 7.55 (m, 3H), 7.90 (m, 2H), 7.98 (m, 2H), 8.42 (m, 1H), 8.46 (d, 1H), 9.66 (s, 1H). MS (+APCI) m/z 492.4 (M+H)$^+$.

Example 6

(1-{[4-(1-Hydroxy-isopropyl)phenyl]methyl]-3-(phenylmethoxy)indol-2-yl}-N-(3-pyridyl) formamide (Compound 136)

Into a 50 mL round bottom flask was placed the above benzoate (example 5) (100 mg) along with THF (10 mL) and, to this stirred solution, was added MeMgCl (0.4 mL, 3.0 M solution in THF) and allowed to stir at room temperature for four hours. At this time, the reaction mixture was quenched by the addition of 10 mL of a saturated aqueous NH$_4$Cl solution and this mixture was poured into a separatory funnel containing 50 mL H$_2$O/50 mL EtOAc. The layers were separated, the aqueous layer was extracted with EtOAc (50 mL) and the combined organic layers were washed with brine, dried over anhydrous MgSO$_4$ and concentrated. The collected material was further purified by flash chromatography eluting with 50% EtOAc/hexanes to provide the title alcohol (30 mg) as a light yellow solid.

$^1$H NMR (acetone-$d_6$) δ 1.42 (s, 6H), 5.60 (s, 2H), 5.97 (s, 2H), 7.05 (d, 2H), 7.18 (m, 1H), 7.25 (m, 1H), 7.57 (m, 3H), 7.97 (m, 2H), 8.24 (m, 1H), 8.49 (d, 1H), 9.67 (s, 1H). MS (+APCI) m/z 492.5 (M+H)$^+$.

Example 7

{1-[(4-Methylphenyl)methyl]-3-(phenylmethoxy) indol-2-yl}-N-(3-pyridyl)formamide (Compound 73)

Following the procedure describing the preparation of example 6, methyl 3-(phenylmethoxy)indole-2-carboxylate (100 mg) in DMF (5.0 mL) was treated with 12 mg of a NaH suspension (60% in oil) followed by 4-methybenzyl bromide (100 mL). After work-up the crude alkylated material was taken up in dry THF (10 mL) and treated with the lithium 3-pyridylamide (0.3 M in THF) solution as described previously. Following work-up and purification by flash chromatography the title indole (58.7 mg) was obtained as a white solid.

$^1$H NMR (acetone-$d_6$) δ 2.22 (s, 3H), 5.59 (s, 2H), 5.94 (s, 2H), 7.01 (m, 4H), 7.16 (m, 1H), 7.25 (m, 1H), 7.38 (m, 1H), 7.53 (m, 3H), 7.99 (m, 2H), 8.23 (m, 1H), 8.49 (d, 1H), 9.65 (s, 1H).

Example 8

(1-{[4-(Tert-butyl)phenyl]methyl}-3-(phenylmethoxy)indol-2-yl]-N-(3-pyridyl) formamide (Compound 172)

Into a round bottom flask was placed methyl 3-(phenylmethoxy)indole-2-carboxylate (50 mg) along with DMF (1.0 mL), THF (1.0 mL) and 10 mg of a NaH suspension (60% in oil). To this stirred mixture was added 4-tert-butylbenzyl bromide and allowed to stir at room temperature overnight. At this time, the reaction mixture was diluted with H$_2$O, poured into a teflon fritted cartridge and extracted with CH$_2$Cl$_2$. The filtrate was concentrated and then treated with THF/H$_2$O (5.0 mL, 1:1), MeOH (2.0 mL), NaOH (1 mL of a 1N aq. solution) and allowed to stir at room temperature overnight. At this time, the reaction mixture was acidified to pH 4 with an aqueous 1N HCl solution, diluted with 2 mL H$_2$O, extracted with CH$_2$Cl$_2$ through a teflon fritted cartridge as above and the filtrate was concentrated. The resulting crude carboxylic acid was taken up in THF (2.0 mL) and treated with i-Pr$_2$NEt (0.1 mL), MsCl (10 μL) followed by 3-aminopyridine (50 mg) as described previously for the preparation of example 166. After work-up and purification by flash chromatography 10.6 mg of the title amide was isolated.

$^1$H NMR (acetone-$d_6$) δ 1.22 (s, 9H), 5.59 (s, 2H), 5.96 (s, 2H), 7.05 (m, 2H), 7.17 (m, 1H), 7.32 (m, 7H), 7.57 (m, 3H), 7.97 (m, 2H), 8.24 (m, 1H), 8.49 (d, 1H), 9.68 (s, 1H). MS (+APCI) m/z 490.6 (M+H)$^+$.

Example 9

(1-{[4-(Trifluormethyl)phenyl]methyl}-3-(phenylmethoxy)indol-2-yl)-N-(3-pyridyl)formamide (Compound 148)

Following the experimental procedure describing the preparation of example 193, 9.8 mg of the title amide was isolated.

$^1$H NMR (acetone-$d_6$) δ 5.63 (s, 2H), 6.08 (s, 2H), 7.24 (m, 4H), 7.36 (m, 4H), 7.57 (m, 5H), 7.97 (m, 1H), 8.23 (d, 1H), 8.25 (d, 1H), 8.46 (d, 1H), 9.67 (s, 1H). MS (+APCI) m/z 502.4 (M+H)$^+$.

Example 10

(1-{[4-(Difluoromethoxy)phenyl]methyl}-3-(phenylmethoxy)indol-2-yl)-N-(3-pyridyl)formamide (Compound 16)

Following the general procedure describing the preparation of example 8,3-(phenylmethoxy)indole-2-carboxylate (100 mg) in DMF (2.0 mL) was treated with 10 mg of a NaH suspension (60% in oil) followed by 4-(difluoromethoxy) benzyl bromide (120 mL). After work-up the crude alkylated material was taken up in THF (5.0 mL) and treated with excess lithium 3-pyridylamide (0.3 M in TBF). Following the usual work-up and purification as described previously, the title amide (50.6 mg) was obtained as a white solid.

$^1$H NMR (acetone-$d_6$) δ 5.59 (s, 2H), 5.96 (s, 2H), 7.06–6.70 (m, 3H), 7.17 (m, 3H), 7.25 (m, 1H), 7.35 (m, 4H), 7.55 (m, 3H), 7.96 (m, 2H), 8.24 (m, 1H), 8.48 (d, 1H), 9.66 (s, 1H). MS (+APCI) m/z 500.5 (M+H)$^+$.

Example 11

{3-(Cyclopropylmethoxy)-1-[(4-fluorophenyl)methyl]indol-2-yl }-N-(3-pyridyl)formamide (Compound 154)

Step 1: {1-[(4-Fluorophenyl)methyl]-3-methoxyindol-2-yl}-N-(3-pyridyl)formamide

A solution containing 102 mg of methyl 1-[(4-fluorophenyl)methyl]-3-hydroxyindole-2-carboxylate, 74 mg of MeOH and 152 mg of di-tert-butyl azodicarboxylate in 1.2 mL of THF and 0.6 mL of CH$_2$Cl$_2$ was treated dropwise with a solution containing 171 mg of triphenylphosphine in 0.6 mL of CH$_2$Cl$_2$. The resulting reaction mixture was stirred overnight at room temperature. The organic solvents were removed under vacuum and the crude mixture was treated with 11 mL of a solution of lithium 3-pyridylamide (0.3 M in THF). The organic solvents were removed under vacuum, CH$_2$Cl$_2$ was added and the organic phase was washed 3 times with aqueous acetic acid (0.05 M). The desired material was extracted with a cartridge filled with 500 mg of sulphonic acid resin (Varian SCX). The resin was washed with MeOH and the desired material was recovered by neutralizing the resin with 5% NH$_4$OH in MeOH. The organic phase was concentrated and filtered over a pad of silica gel eluting with ethyl acetate. The filtrate was concentrated to dryness and the resulting solid was recrystallized with a ethyl acetate/hexane mixture to give 54 mg of the title compound as off-white solid.

$^1$H NMR (acetone-$d_6$) δ 4.37 (s, 3H), 5.97 (s, 2H), 7.00 (t, 2H), 7.15 (t, 1H), 7.21 (dd, 2H), 7.34 (m, 2H), 7.57 (d, 1H), 7.92 (d, 1H), 8.25 (dd, 1H), 8.30 (dd, 1H), 8.86 (dd, 1H), 9.79 (s, 1H). MS (+APCI) m/z 377.4 (M+H)$^+$.

Step 2:

The title compound was prepared from 102 mg of methyl 1-[(4-fluorophenyl)methyl]-3-hydroxyindole-2-carboxylate and 50 mg of cyclopropanemethanol according to example 164 to yield 111 mg of a yellow solid.

$^1$H NMR (acetone-$d_6$) δ 0.43 (m, 2H), 0.65 (m, 2H), 1.46 (m, 1H), 4.41 (d, 2H), 5.98 (s, 2H), 7.00 (t, 2H), 7.14 (t, 1H), 7.21 (dd, 2H), 7.34 (m, 2H), 7,56 (d, 1H), 7.85 (d, 1H), 8.29 (m, 2H), 8.88 (d, 1H), 10.08 (s, 1H). MS (+APCI) m/z 416.4 (M+H)$^+$.

Example 12

{1-[(4-Fluorophenyl)methyl]-3-(4-pyridylmethoxy)indol-2-yl}-N-(3-pyridyl)formamide (Compound 162)

The title compound was prepared from 102 mg of methyl 1-[(4-fluorophenyl)methyl]-3-hydroxyindole-2-carboxylate and 59 mg of 4-pyridyl carbinol according to example 11, step 1, to yield 56 mg of a red solid.

$^1$H NMR (acetone-$d_6$) δ 5.63 (s, 2H), 5.94 (s, 2H), 7.01 (t, 2H), 7.18 (m, 3H), 7.30 (dd, 1H), 7.35 (t, 1H), 7.54 (d, 2H), 7.59 (d, 1H), 7.89 (d, 1H), 8.08 (dt, 1H), 8.28 (dd, 1H), 8.60 (dd, 2H), 8.65 (d, 1H), 9.62 (s, 1H). MS (+APCI) m/z 453.3 (M+H)$^+$.

Example 13

{1-[(4-Fluorophenyl)methyl]-3-[(3-methoxyphenyl)methoxy]indol-2-yl}-N-(3-pyridal)formamide (Compound 22)

The title compound was prepared from 102 mg of methyl 1-[(4-fluorophenyl)methyl]-3-hydroxyindole-2-carboxylate and 94 mg of 3-methoxybenzyl alcohol according to example 164 to yield 63 mg of a white solid.

$^1$H NMR (acetone-$d_6$) δ 5.57 (s, 2H), 5.96 (s, 2H), 6.94 (dd, 1H), 7.00 (t, 2H), 7.05–7.25 (m, 51), 7.28 (m, 2H), 7.35 (t, 1H), 7.58 (d, 1H), 7.98 (t, 2H), 8.25 (dd, 1H), 8.52 (d, 1H), 9.66 (s, 1H). MS (+APCI) m/z 482.3 (M+H)$^+$.

Example 14

{5-Bromo-1-[(4-fluorophenyl)methyl]-3-(phenylmethoxy)indol-2-yl}-N-(3-pyridal)formamide (Compound 134)

Step 1: Ethyl 5-Bromo-3-formylindole-2-carboxylate

In a 1 L round bottom flask 10.5 mL of phosphorus oxychloride was added to 15.5 g of N-methylformanilide at room temperature that resulted in a yellow solid after 15 min. At this time, 170 mL of 1,2-dichloroethane and 20.1 g of ethyl 5-bromoindole-2-carboxylate were added. The resulting suspension was heated under reflux for 4 hours and then concentrated to remove the organic solvent. 75 g of sodium acetate in 750 mL of water were added and the solid suspension was stirred for 30 min at room temperature, filtered and washed 3 times with water. The crude material was dried under vacuum for 1 hour and swished with 500 mL of EtOH to yield 21.2 g of the title compound as off-white solid.

$^1$H NMR (acetone-$d_6$) δ 1.43 (t, 3H), 5.50 (q, 2H), 7.52 (dd, 1H), 7.58 (d, 1H), 8.52 (d, 1H), 10.68 (s, 1H), 11.86 (s, 1H).

Step 2: Ethyl 5-Bromo-3-hydroxyindole-2-carboxylate

A mixture of 21.24 g of the previous aldehyde and 14.42 g of p-toluenesuphonic acid monohydrate in 1 L of CH$_2$Cl$_2$ was maintained at 12–13° C. and treated portionwise with 17.01 g of dried 3-chloroperoxybenzoic acid (87% purity). The reaction mixture was stirred at this temperature for 2.5 hours (reaction was monitored by TLC), quenched with 3 mL of dimethyl sulfide and poured 30 min later into a saturated aqueous bicarbonate solution. The product was extracted with $CH_2Cl_2$, washed twice with saturated aqueous bicarbonate, brine and dried over anhydrous $Na_2SO_4$. The organic solvent was removed under vacuum and the crude material was hydrolyzed by treatment with 10 mL of $Et_3N$ in 300 mL of EtOH and heating to 70° C. for 30 min. The organic solvent was removed under vacuum and the crude material was dissolved in ethyl acetate and washed twice with 0.5 N HCl, brine and dried over anhydrous $Na_2SO_4$. The organic phase was concentrated and filtered over a pad of silica gel eluting with hot toluene. The organic phase was concentrated to dryness and the solid was swished with ethyl acetate and hexane to give 18.14 g of the title compound as a grey solid (>97% purity).

$^1$H NMR (acetone-$d_6$) δ 1.35 (t, 3H), 4.39 (q, 2H), 7.35 (dd, 1H), 7.39 (dd, 1H), 7.79 (t, 1H), 8.24 (s, 1H), 10.23 (s, 1H).

Step 3: Ethyl 5-Bromo-3-(phenylmethoxy)indole-2-carboxylate

To a solution containing 2.04 g of ethyl 5-bromo-3-hydroxyindole-2-carboxylate, 3.94 g of benzyl alcohol and 3.34 g of di-tert-butyl azodicarboxylate in 30 mL of THF and 15 mL of $CH_2Cl_2$ at −78° C. was treated dropwise with a solution containing 3.81 g of triphenylphosphine in 15 mL of $CH_2Cl_2$. The resulting reaction mixture was warmed slowly to 0° C. upon consumption of the starting material (monitored by TLC). 800 μL of acetic acid was added and after 30 min the solvents were removed under vacuum and the excess of acetic acid was removed by coevaporation with toluene. The crude product was filtered over a pad of silica gel eluting with $CH_2Cl_2$. The organic phase was concentrated to dryness and the solid was swished with hexane to give 2.13 g of the title compound as a white solid.

$^1$H NMR (acetone-$d_6$) δ 1.36 (t, 3H), 4.38 (q, 2H), 5.30 (s, 2H), 7.30–7.40 (m, 5H), 7.56 (d, 2H), 7.76 (d, 1H), 10.56 (s, 1H). MS (+APCI) m/z 376.2, 374.1 (M+H)$^+$.

Step 4: Ethyl 5-Bromo-1-[(4-fluorophenyl)methyl]-3-(phenylmethoxy)indole-2-carboxylate To a mixture of 5.57 g of ethyl 5-bromo-3-(phenylmethoxy)indole-2-carboxylate and 2.9 mL of 4-fluorobenzyl bromide in 40 mL of DMF at 0° C. was added 887 mg of a NaH suspension (60% in oil) and the resulting reaction mixture was warmed slowly to room temperature with continuous stirring. After 0.5 hour, the reaction was quenched with saturated aqueous $NH_4Cl$ and extracted twice with ethyl acetate/ether 1:1. The organic phase was washed with water (4×), brine and dried over anhydrous $Na_2SO_4$. Flash chromatography (toluene) and recrystallization from hexane yielded 5.99 g of the title compound as a white solid.

$^1$H NMR (acetone-$d_6$) δ 1.29 (t, 3H), 4.33 (q, 2H), 5.26 (s, 2H), 5.79 (s, 2H), 7.00–7.10 (m, 4H), 7.30–7.40 (m, 4H), 7.51 (m, 3H), 7.78 (s, 1H). MS (+APCI) m/z 484.3, 482.2 (M+H)$^+$.

Step 5: {5-Bromo-1-[(4-fluorophenyl)methyl]-3-(phenylmethoxy)indol-2-yl}-N-(3-pyridyl)formamide To a solution of 1.06 g of the above ester in 5 mL of THF 40 mL of a solution of lithium 3-pyridylamide (0.3 M in THF) was added and allowed to stir at room temperature. After consumption of the starting ester, the organic solvents were removed under vacuum, aqueous acetic acid (0.05 M) was added and the product was extracted with ethyl acetate. The organic layer was washed 3 times with aqueous acetic acid (0.05 M), water (3×), brine and dried over anhydrous $Na_2SO_4$. The organic phase was concentrated and filtered over a pad of silica gel eluting with ethyl acetate. The organic phase was concentrated to dryness and the solid was swished with ethyl acetate and hexane to give 1.16 g of the title compound as a white solid.

$^1$H NMR (acetone-$d_6$) δ 5.58 (s, 2H), 5.95 (s, 2H), 7.01 (td, 2H), 7.17 (dd, 2H), 7.27 (dd, 1H), 7.38 (m, 3H), 7.44 (dd, 1H), 7.55 (m, 3H), 7.97 (m, 1H), 8.11 (d, 1H), 8.27 (dd, 1H), 8.50 (d, 1H), 9.62 (s, 1H). MS (+APCI) m/z 532.3, 530.2 (M+H)$^+$. Anal. Calcd for $C_{28}H_{21}BrFN_3O_2$: C, 63.41; H, 3.99; N, 7.92. Found: C, 63.12; H, 4.31; N, 7.98.

Example 15

{1-[(4-Fluorophenyl)methyl]-5-(1-hydroxy-isopropyl)-3-(phenylmethoxy)indol-2-yl}-N-(3-pyridyl)formamide (Compound 130)

To a solution of 201 mg of {5-Bromo-1-[(4-fluorophenyl)methyl]-3-(phenylmethoxy)indol-2-yl}-N-(3-pyridyl)formamide in 10 mL of THF at −100° C. was added 0.5 mL of n-BuLi (1.6 M in hexanes) and the mixture was stirred at −100° C. for 30 min. To this cold solution, 190 μL of acetone was added and the reaction mixture was allowed to warm to room temperature. At this time, aqueous $NH_4Cl$ was added, the product was extracted with ethyl acetate and the organic phase was washed with brine and dried over anhydrous $Na_2SO_4$. Flash chromatography (100% hexane to hexane/ethyl acetate 1:2) and swish with $CH_2Cl_2$/hexane yielded 61 mg of the title compound as a yellow solid.

$^1$H NMR (acetone-$d_6$) δ 1.58 (s, 6H), 4.14 (s, 1H), 5.59 (s, 2H), 5.93 (s, 2H), 7.00 (t, 2H), 7.18 (m, 2H), 7.24 (dd, 1H), 7.38 (m, 3H), 7.45–7.55 (m, 4H), 7.95 (d, 1H), 8.08 (dd, 1H), 8.24 (dd, 1H), 8.46 (d, 1H), 9.65 (s, 1H). MS (+APCI) m/z 510.4 (M+H)$^+$.

Example 16

1-[(4-Fluorophenyl)methyl]-3-(phenylmethoxy)-2-(N-(3-pyridyl)carbamoyl)indole-5-carboxylic Acid (Compound 131)

To a solution of 201 mg of {5-Bromo-1-[(4-fluorophenyl)methyl]-3-(phenylmethoxy)indol-2-yl}-N-(3-pyridyl)formamide in 10 mL of THF at −100° C. was added 0.5 mL of n-BuLi (1.6 M in hexanes) and the mixture was stirred at −100° C. for 30 min. $CO_2$ was introduced to the reaction mixture and warmed to room temperature. The reaction was quenched with 150 μL of acetic acid and poured into a saturated aqueous $NH_4Cl$ solution. The product was extracted with ethyl acetate and the organic phase was washed with brine and dried over anhydrous $Na_2SO_4$. The organic phase was concentrated and the crude solid was swished with ethyl acetate to give 75 mg of the title compound as a white solid (>95% purity).

$^1$H NMR (dmso-$d_6$) δ 5.42 (s, 2H), 5.76 (s, 2H), 7.08 (m, 4H), 7.25–7.35 (m, 4H), 7.40 (d, 2H), 7.69 (d, 1H), 7.87 (d, 1H), 7.98 (d, 1H), 8.28 (d, 1H), 8.46 (s, 1H), 8.61 (s, 1H), 10.12 (s, 1H), 12.76 (s, 1H). MS (+APCI) m/z 496.5 (M+H)$^+$.

Example 17

{1-[(4-Fluorophenyl)methyl]-4-(1-hydroxy-isopropyl)-3-(phenylmethoxy)indol-2-yl}-N-(3-pyridyl)formamide (Compound 94)

Step 1: Ethyl 4-Bromo-indolecarboxylate

A solution of 23 mL of ethyl azidoacetate and 7.6 mL of 2-bromobenzaldehyde in 40 mL ethanol was added dropwise to a solution of 4.5 g sodium in 180 mL ethanol, in a bath at −10° C., at a rate such that the reaction temperature does not rise above 8° C. After the addition is complete, the mixture is stirred at 5–10° C. for 30 min. The reaction mixture is then poured into a mixture of 28 g of $NH_4Cl$ in 1 L ice, and extracted with 1:4 $CH_2Cl_2$hexane. The organic phase is filtered through 150 mL silica gel, which is rinsed with 200 mL of the same solvent. This is evaporated to near dryness, diluted with 300 mL xylene, and stabilised with 60 mg of 2,5-di-t-butylhydroquinone. This mixture is heated with a distillation head until 50 mL of xylene has distilled. The mixture is cooled and evaporated in vacuo to a volume of 80 mL, which is diluted with 80 mL of hexane. A white solid forms upon cooling to 0° C., which is filtered off.

$^1$H NMR (acetone-$d_6$) δ 1.37 (t, 3H), 4.37 (q, 2H), 7.13 (t, 1H), 7.21 (t, 1H), 7.33 (d, 1H), 7.55 (d, 1H), 11.3 (s, 1H).

Example 18

{1-[(4-Fluorophenyl)methyl]-6-(1-hydroxy-isopropyl)-3-(phenylmetoxy)indol-2-yl}-N-(3-pyridyl)formamide (Compound 118)

Step 1: Ethyl 6-Bromo-indolecarboxylate

Using the method described in example 17, Step 1, starting with 4-bromobenzaldehyde, the title compound is obtained as a white solid.

$^1$H NMR (acetone-$d_6$) δ 1.35 (t, 3H), 4.35 (q, 2H), 7.18 (s, 1H), 7.24 (d, 1H), 7.64 (d, 1H), 7.73 (s, 1H), 11.10 (s, 1H).

What is claimed is:

1. A compound represented by formula I:

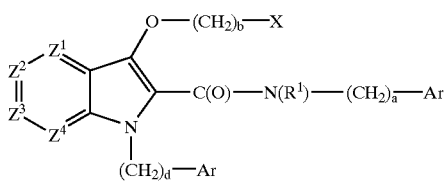

or a pharmaceutically acceptable salt or hydrate thereof wherein:
one of $Z^1$, $Z^2$, $Z^3$ and $Z^4$ represents N or $CR^2$ and the others represent $CR^2$;
a represents 0 or 1;
b represents 0, 1 or 2;
d represents 1;
$R^1$ represents H, $C_{1-4}$alkyl or hydroxy$C_{1-4}$alkyl;
each $R^2$ is independently selected from the group consisting of:
H, halo, $C_{1-8}$alkyl, halo$C_{1-8}$alkyl, hydroxy$C_{1-8}$alkyl, CN, Het, $OR^a$, $OC(O)N(R^b)_2$, $NR^bC(O)R^a$, $C(R^a)_2CO_2R^a$, $C_{1-8}$alkyl$N(R^b)_2$, halo$C_{1-8}$alkyl$N(R^b)_2$, $CO_2R^a$, $C(O)N(R^b)_2$, $SO_2N(R^b)_2$, $S(O)_bR^d$ and $NR^bSO_2R^d$;
each $R^a$ is independently selected from H, $C_{1-4}$alkyl, $C_{1-4}$alkylNH$C_{1-4}$alkyl, and $C_{1-4}$alkylN($C_{1-4}$alkyl)$_2$, the alkyl portions of which are optionally substituted with 1–3 halo groups;
each $R^b$ is selected from H and $C_{1-7}$alkyl, and when two $R^b$'s are present, they can be taken together and represent a fused ring system having 5–10 members, said ring system being saturated or containing 1–4 double bonds, and optionally including 1–3 heteroatoms selected from O, S and $NR^e$;
$R^d$ and $R^e$ are independently selected from Het, $C^{1-7}$alkyl, $C^{2-7}$alkenyl, $C_{2-7}$alkynyl, and $C_{1-7}$alkyl-Het;
Het represents a 5–10 membered aromatic, partially aromatic or non-aromatic ring system containing 1–4 heteroatoms selected from O, S and N, optionally substituted on any available position with oxo, $C_{1-4}$alkyl, halo, amino, hydroxy$C_{1-4}$ alkyl, halo$C_{1-4}$alkyl and amino$C_{1-4}$alkyl;
X represents $C_{3-7}$cycloalkyl or Ar;
and each Ar is independently selected from the group consisting of: phenyl, thienyl, thiazolyl, pyridyl, oxazolyl, tetrazolyl, pyrimidinyl, pyrazinyl and pyridazinyl,
said Ar being optionally substituted with 1–4 members selected from: halo, hydroxy, CN, $C_{1-4}$alkyl, $C_{1-6}$haloalkyl, $C_{1-6}$hydroxyalkyl, $OC_{1-6}$alkyl, $OC_{1-6}$haloalkyl, $OC_{1-6}$hydroxyalkyl, $C_{1-6}$alkyl $OC_{1-6}$alkyl, $C_{1-6}$alkyl$OC_{1-6}$haloalky $C(O)NH_2$, $C(O)NHC_{1-6}$alkyl, $C(O)N(C_{1-6}$alkyl)$_2$, $C_{1-6}$alkyl $OC_{1-6}$alkyl$C(O)NH_2$, $CO_2H$, $CO_2C_{1-6}$alkyl, $NHC(O)C_{1-6}$alkyl, $NHC(O)OC_{1-6}$alkyl, and $SO_2C_{1-6}$alkyl.

2. A compound in accordance with claim 1 wherein $Z^1$, $Z^2$, $Z^3$ and $Z^4$ represent $CR^2$.

3. A compound in accordance with claim 1 wherein b represents 0 or 1.

4. A compound in accordance with claim 1 wherein $R^1$ represents H or $CH_3$.

5. A compound in accordance with claim 1 wherein each $R^2$ is independently selected from the group consisting of H, $C_{1-8}$alkyl, hydroxy$C_{1-8}$alkyl, $CO_2R^a$, $C_{1-8}$alkyl$N(R^b)_2$ and $C(O)N(R^b)_2$;
and $R^b$ is selected from H and $C_{1-3}$alkyl.

6. A compound in accordance with claim 1 wherein X represents Ar and Ar is independently selected from the group consisting of: phenyl, pyridyl and tetrazolyl,
said Ar being optionally substituted with 1–4 members selected from:

halo, CN, $C_{1-4}$alkyl, $C_{1-6}$haloalkyl, $OC_{1-6}$alkyl, $OC_{1-6}$haloalkyl, $C_{1-6}$hydroxyalkyl, $C(O)NH_2$, $C(O)NHC_{1-6}$alkyl, $C(O)N(C_{1-6}$alkyl)$_2$, $CO_2H$, $CO_2C_{1-6}$alkyl, $NHC(O)C_{1-6}$alkyl, $NHC(O)OC_{1-6}$alkyl and $SO_2C_{1-6}$alkyl.

7. A compound in accordance with claim 1 wherein:

$Z^1$, $Z^2$, $Z^3$ and $Z^4$ represent $CR^2$;
each $R^2$ is independently selected from the group consisting of H, $C_{1-8}$alkyl, hydroxy$C_{1-8}$alkyl, $CO_2R^a$, $C_{1-8}$alkyl$N(R^b)_2$ and $C(O)N(R^b)_2$ wherein $R^b$ is selected from H and $C_{1-3}$alkyl;
b represents 0 or 1;
d represents 1;
$R^1$ represents H or $CH_3$;
X represents Ar and
Ar is independently selected from the group consisting of: phenyl, pyridyl and tetrazolyl, said Ar being optionally substituted with 1–4 members selected from: halo, CN, $C_{1-4}$alkyl, $C_{1-6}$haloalkyl, $OC_{1-6}$alkyl, $OC_{1-6}$haloalkyl, $C_{1-6}$hydroxyalkyl, $C(O)NH_2$, $C(O)NHC_{1-6}$alkyl, $C(O)N(C_{1-6}$alkyl)$_2$, $CO_2H$, $CO_2C_{1-6}$alkyl, $NHC(O)C_{1-6}$alkyl, $NHC(O)OC_{1-6}$alkyl and $SO_2C_{1-6}$alkyl.

8. A compound represented by Formula Ia:

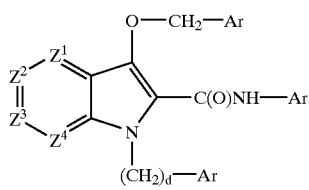

Ia wherein all variables are as defined in claim 1.

9. A compound in accordance with claim 8 wherein $Z^1$, $Z^2$, $Z^3$ and $Z^4$ represent $CR^2$.

10. A compound in accordance with claim 8 wherein each $R^2$ is independently selected from the group consisting of H, $C_{1-8}$alkyl, hydroxy$C_{1-8}$alkyl, $CO_2R^a$, $C_{1-8}$alkylN($R^b$)$_2$ and $C(O)N(R^b)_2$ wherein $R^a$ is independently selected H and $C_{1-4}$alkyl, and $R^b$ is selected from H and $C_{1-3}$alkyl.

11. A compound in accordance with claim 8 wherein each Ar is selected from phenyl, pyridyl and tetrazolyl, optionally substituted with 1–4 members selected from: halo, CN, $C_{1-4}$alkyl, $C_{1-6}$haloalkyl, $OC_{1-6}$alkyl, $OC_{1-6}$haloalkyl, $C_{1-6}$hydroxyalkyl, $C(O)NH_2$, $C(O)NHC_{1-6}$alkyl, $C(O)N(C_{1-6}$alkyl)$_2$, $CO_2H$, $CO_2C_{1-6}$alkyl, $NHC(O)C_{1-6}$alkyl, $NHC(O)OC_{1-6}$alkyl and $SO_2C_{1-6}$alkyl.

12. A compound in accordance with claim 1 in accordance with the following table:

| Cpd | Z's | —(O)—(CH$_2$)$_b$—X | N(R$^1$)(CH$_2$)$_a$—Ar | (CH$_2$)$_d$-Ar |
|---|---|---|---|---|
| 1 | CH | OCH$_2$-Phe-4-F | N(Me)-3-Pyr | Bnzl |
| 2 | CH | OCH$_2$-Phe-4-F | N(Me)-4-Pyr | Bnzl |
| 3 | CH | OCH$_2$-Phe-4-F | N(Me)-Phe-3,4-di-OMe | Bnzl |
| 4 | CH | OCH$_2$-Phe-4-F | N(Me)-Phe-3,4-di-F | Bnzl |
| 5 | CH | OCH$_2$-Phe-4-F | N(Me)-5-Pyr-2-OMe | Bnzl |
| 6 | CH | OCH$_2$-Phe-4-F | N(Me)-5-tetrazolyl | Bnzl |
| 7 | CH | OCH$_2$-Phe-4-F | N(Me)-4-Pyr-2-OMe | Bnzl |
| 8 | CH | OCH$_2$-Phe-4-F | N(Me)-5-Pyr-2-CN | Bnzl |
| 9 | CH | OCH$_2$-Phe-4-F | N(Me)-4-Pyr-2-OMe | Bnzl |
| 10 | CH | O-Bnzl | NH-Phe-3,4-di-OMe | Bnzl-4-F |
| 11 | CH | O-Bnzl | NH-3-Pyr | Bnzl-4-F |
| 12 | CH | OCH$_2$-Phe-3-OCF$_2$H | NH-3-Pyr | Bnzl-3-OCF$_2$H |
| 13 | CH | OCH$_2$-Phe-3-OCF$_2$H | NH-4-Pyr | Bnzl-3-OCF$_2$H |
| 14 | CH | OCH$_2$-Phe-3-OCF$_2$H | NH-Phe-3,4-di-OMe | Bnzl-3-OCF$_2$H |
| 15 | CH | OCH$_2$-Phe-3-OCF$_2$H | NH-Phe-3,4-di-F | Bnzl-3-OCF$_2$H |
| 16 | CH | O-Bnzl | NH-3-Pyr | Bnzl-4-OCF$_2$H |
| 17 | CH | OCH$_2$-Phe-3-OMe | NH-3-Pyr | Bnzl-4-OCF$_2$H |
| 18 | CH | OCH$_2$-Phe-3-OMe | NH-5-tetrazolyl | Bnzl-4-OCF$_2$H |
| 19 | CH | OCH$_2$-Phe-3-OMe | NH-4-Pyr-2-OMe | Bnzl-4-OCF$_2$H |
| 20 | CH | OCH$_2$-Phe-3-OMe | NH-4-Pyr | Bnzl-4-OCF$_2$H |
| 21 | CH | OCH$_2$-Phe-3-OMe | NH-4-Pyr-2-NHC(O)Me | Bnzl-4-OCF$_2$H |
| 22 | CH | OCH$_2$-Phe-3-OMe | NH-3-Pyr | Bnzl-4-F |
| 23 | CH | OCH$_2$-Phe-3-OMe | NH-5-tetrazolyl | Bnzl-4-F |
| 24 | CH | OCH$_2$-Phe-3-OMe | NH-4-Pyr-2-OMe | Bnzl-4-F |
| 25 | CH | OCH$_2$-Phe-3-OMe | NR-4-Pyr | Bnzl-4-F |

-continued $$\text{I}$$

Structure I: pyrrole core fused with Z$^1$-Z$^2$-Z$^3$-Z$^4$ ring, with O—(CH$_2$)$_b$—X at 3-position, C(O)—N(R$^1$)—(CH$_2$)$_a$—Ar at 2-position, and (CH$_2$)$_d$—Ar on N.

| Cpd | Z's | —(O)—(CH$_2$)$_b$—X | N(R$^1$)(CH$_2$)$_a$—Ar | (CH$_2$)$_d$-Ar |
|---|---|---|---|---|
| 26 | CH | OCH$_2$-Phe-3-OMe | NH-4-Pyr-2-NHC(O)Me | Bnzl-4-F |
| 27 | CH | OCH$_2$-Phe-3-OMe | NH-5-pyrimidinyl | Bnzl-4-F |
| 28 | CH | O-Bnzl | NH-3-Pyr | Bnzl-3,4-di-F |
| 29 | CH | O-Bnzl | NH-4-Pyr | Bnzl-3,4-di-F |
| 30 | CH | O-Bnzl | NH-Phe-3,4-di-OMe | Bnzl-3,4-di-F |
| 31 | CH | O-Bnzl | NH-Phe-3,4-di-F | Bnzl-3,4-di-F |
| 32 | CH | O-Bnzl | NH-5-Pyr-2-OMe | Bnzl-3,4-di-F |
| 33 | CH | O-Bnzl | NH-5-tetrazolyl | Bnzl-3,4-di-F |
| 34 | CH | O-Bnzl | NH-4-Pyr-2-OMe | Bnzl-3,4-di-F |
| 35 | CH | O-Bnzl | NH-5-Pyr-2-CN | Bnzl-3,4-di-F |
| 36 | CH | O-Bnzl | NH-5-Pyr-2-NHC(O)Me | Bnzl-3,4-di-F |
| 37 | CH | OCH$_2$-4-Pyr | NH-3-Pyr | Bnzl-4-CF$_3$ |
| 38 | CH | OCH$_2$-4-Pyr | NH-4-Pyr | Bnzl-4-CF$_3$ |
| 39 | CH | OCH$_2$-4-Pyr | NH-Phe-3,4-di-OMe | Bnzl-4-CF$_3$ |
| 40 | CH | OCH$_2$-4-Pyr | NH-Phe-3,4-di-F | Bnzl-4-CF$_3$ |
| 41 | CH | OCH$_2$-4-Pyr | NH-5-Pyr-2-OMe | Bnzl-4-CF$_3$ |
| 42 | CH | OCH$_2$-4-Pyr | NH-5-tetrazolyl | Bnzl-4-CF$_3$ |
| 43 | CH | OCH$_2$-4-Pyr | NH-4-Pyr-2-OMe | Bnzl-4-CF$_3$ |
| 44 | CH | OCH$_2$-4-Pyr | NH-5-Pyr-2-CN | Bnzl-4-CF$_3$ |
| 45 | CH | OCH$_2$-4-Pyr | NH-5-Pyr-2-NHC(O)Me | Bnzl-4-CF$_3$ |
| 46 | CH | OCH$_2$-4-Pyr | NH-3-Pyr | Bnzl |
| 47 | CH | OCH$_2$-4-Pyr | NH-4-Pyr | Bnzl |
| 48 | CH | OCH$_2$-4-Pyr | NH-Phe-3,4-di-OMe | Bnzl |
| 49 | CH | OCH$_2$-4-Pyr | NH-Phe-3,4-di-F | Bnzl |
| 50 | CH | OCH$_2$-4-Pyr | NH-5-Pyr-2-OMe | Bnzl |
| 51 | CH | OCH$_2$-4-Pyr | NH-5-tetrazolyl | Bnzl |
| 52 | CH | OCH$_2$-4-Pyr | NH-4-Pyr-2-OMe | Bnzl |
| 53 | CH | OCH$_2$-4-Pyr | NH-5-Pyr-2-CN | Bnzl |
| 54 | CH | OCH$_2$-4-Pyr | NH-5-Pyr-2-NHC(O)Me | Bnzl |
| 55 | CH | OCH$_2$-4-Pyr | NH-4-Pyr-2-NHC(O)OEt | Bnzl |
| 56 | CH | O-Bnzl | NH-3-Pyr | Bnzl |
| 57 | CH | O-Bnzl | NH-4-Pyr | Bnzl |
| 58 | CH | O-Bnzl | NH-Phe-3,4-di-OMe | Bnzl |
| 59 | Z$^1$ = N, all others = CH | O-Bnzl | NH-Phe-3,4-di-F | Bnzl |
| 60 | Z$^1$ = N, all others = CH | O-Bnzl | NH-5-Pyr-2-OMe | Bnzl |
| 61 | CH | O-Bnzl | NH-5-tetrazolyl | Bnzl |
| 62 | CH | O-Bnzl | NH-4-Pyr-2-OMe | Bnzl |
| 63 | CH | O-Bnzl | NH-5-Pyr-2-CN | Bnzl |
| 64 | CH | O-Bnzl | NH-5-Pyr-2-NHC(O)Me | Bnzl |

-continued

I

| Cpd | Z's | —(O)—(CH$_2$)$_b$—X | N(R$^1$)(CH$_2$)$_a$—Ar | (CH$_2$)$_d$-Ar |
|---|---|---|---|---|
| 65 | CH | O-Bnzl | NH-4-Pyr-2-NHC(O)OEt | Bnzl |
| 66 | CH | OCH$_2$-4-Pyr | NH-3-Pyr | Bnzl-4-OCF$_2$H |
| 67 | CH | OCH$_2$-4-Pyr | NH-4-Pyr | Bnzl-4-OCF$_2$H |
| 68 | CH | OCH$_2$-4-Pyr | NH-Phe-3,4-di-OMe | Bnzl-4-OCF$_2$H |
| 69 | CH | OCH$_2$-4-Pyr | NH-Phe-3,4-di-F | Bnzl-4-OCF$_2$H |
| 70 | Z$^1$ = N, all others = CH | OCH$_2$-4-Pyr | NH-5-Pyr-2-OMe | Bnzl-4-OCF$_2$H |
| 71 | Z$^1$ = N, all others = CH | OCH$_2$-4-Pyr | NH-5-tetrazolyl | Bnzl-4-OCF$_2$H |
| 72 | Z$^1$ = N, all others = CH | OCH$_2$-4-Pyr | NH-4-Pyr-2-OMe | Bnzl-4-OCF$_2$H |
| 73 | CH | O-Bnzl | NH-3-Pyr | Bnzl-4-Me |
| 74 | CH | OCH$_2$-4-Pyr | NH-5-Pyr-2-CN | Bnzl-4-OCF$_2$H |
| 75 | CH | OCH$_2$-4-Pyr | NH-5-Pyr-2-NHC(O)Me | Bnzl-4-OCF$_2$H |
| 76 | Z$^4$ = CC(Me)$_2$OH all others = CH | OCH$_2$-4-Pyr | NH-5-tetrazolyl | Bnzl-4-CF$_3$ |
| 77 | Z$^4$ = CCO$_2$H all others = CH | OCH$_2$-4-Pyr | NH-5-tetrazolyl | Bnzl-4-CF$_3$ |
| 78 | Z$^4$ = CCH$_2$NMe$_2$ All others = CH | OCH$_2$-4-Pyr | NH-5-tetrazolyl | Bnzl-4-CF$_3$ |
| 79 | Z$^4$ = CC(O)NMe$_2$ All others = CH | OCH$_2$-4-Pyr | NH-5-tetrazolyl | Bnzl-4-CF$_3$ |
| 80 | Z$^4$ = CBr All others = CH | OCH$_2$-4-Pyr | NH-5-tetrazolyl | Bnzl-4-CF$_3$ |
| 81 | Z$^4$ = CSO$_2$NH$_2$ all others = CH | OCH$_2$-4-Pyr | NH-5-tetrazolyl | Bnzl-4-CF$_3$ |
| 82 | Z$^1$ = CC(Me)$_2$OH all others = CH | OCH$_2$-4-Pyr | NH-5-tetrazolyl | Bnzl-4-CF$_3$ |
| 83 | Z$^1$ = CCO$_2$H all others = CH | OCH$_2$-4-Pyr | NH-5-tetrazolyl | Bnzl-4-CF$_3$ |
| 84 | Z$^1$ = CCH$_2$NMe$_2$ all others = CH | OCH$_2$-4-Pyr | NH-5-tetrazolyl | Bnzl-4-CF$_3$ |
| 85 | Z$^1$ = CC(O)NMe$_2$ all others = CH | OCH$_2$-4-Pyr | NH-5-tetrazolyl | Bnzl-4-CF$_3$ |
| 86 | Z$^1$ = CBr all others = CH | OCH$_2$-4-Pyr | NH-5-tetrazolyl | Bnzl-4-CF$_3$ |
| 87 | Z$^1$ = CSO$_2$NH$_2$ all others = CH | OCH$_2$-4-Pyr | NH-5-tetrazolyl | Bnzl-4-CF$_3$ |
| 88 | Z$^1$ = CC(Me)$_2$OH all others = CH | OCH$_2$-4-Pyr | NH-4-Pyr | Bnzl-4-CF$_3$ |
| 89 | Z$^1$ = CCO$_2$H all others = CH | OCH$_2$-4-Pyr | NH-4-Pyr | Bnzl-4-CF$_3$ |
| 90 | Z$^1$ = CCH$_2$NMe$_2$ all others = CH | OCH$_2$-4-Pyr | NH-4-Pyr | Bnzl-4-CF$_3$ |

-continued

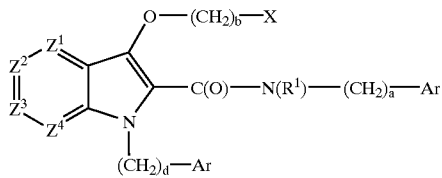

I

| Cpd | Z's | —(O)—(CH$_2$)$_b$—X | N(R$^1$)(CH$_2$)$_a$—Ar | (CH$_2$)$_d$-Ar |
|---|---|---|---|---|
| 91 | Z$^1$ = CC(O)NMe$_2$ all others = CH | OCH$_2$-4-Pyr | NH-4-Pyr | Bnzl-4-CF$_3$ |
| 92 | Z$^1$ =CBr all others = CH | OCH$_2$-4-Pyr | NH-4-Pyr | Bnzl-4-CF$_3$ |
| 93 | Z$^1$ = CSO$_2$NH$_2$ all others = CH | OCH$_2$-4-Pyr | NH-4-Pyr | Bnzl-4-CF$_3$ |
| 94 | Z$^1$ = CC(Me)$_2$OH all others = CH | O-Bnzl | NH-3-Pyr | Bnzl-4-F |
| 95 | Z$^1$ = CCO$_2$H all others = CH | O-Bnzl | NH-3-Pyr | Bnzl-4-F |
| 96 | Z$^1$ = CCH$_2$NMe$_2$ all others = CH | O-Bnzl | NH-3-Pyr | Bnzl-4-F |
| 97 | Z$^1$ = CC(O)NMe$_2$ all others = CH | O-Bnzl | NH-3-Pyr | Bnzl-4-F |
| 98 | Z$^1$ =CBr all others = CH | O-Bnzl | NH-3-Pyr | Bnzl-4-F |
| 99 | Z$^1$ = CSO$_2$NH$_2$ all others = CH | O-Bnzl | NH-3-Pyr | Bnzl-4-F |
| 100 | Z$^4$ = CC(Me)$_2$OH all others = CH | OCH$_2$-4-Pyr | NH-4-Pyr | Bnzl-4-CF$_3$ |
| 101 | Z$^4$ = CCO$_2$H all others = CH | OCH$_2$-4-Pyr | NH-4-Pyr | Bnzl-4-CF$_3$ |
| 102 | Z$^4$ = CCH$_2$NMe$_2$ all others = CH | OCH$_2$-4-Pyr | NH-4-Pyr | Bnzl-4-CF$_3$ |
| 103 | Z$^4$ = CC(O)NMe$_2$ all others = CH | OCH$_2$-4-Pyr | NH-4-Pyr | Bnzl-4-CF$_3$ |
| 104 | Z$^4$ =CBr all others = CH | OCH$_2$-4-Pyr | NH-4-Pyr | Bnzl-4-CF$_3$ |
| 105 | Z$^4$ = CSO$_2$NH$_2$ all others = CH | OCH$_2$-4-Pyr | NH-4-Pyr | Bnzl-4-CF$_3$ |
| 106 | Z$^4$ = CC(Me)$_2$OH all others = CH | O-Bnzl | NH-3-Pyr | Bnzl-4-F |
| 107 | Z$^4$ = CCO$_2$H all others = CH | O-Bnzl | NH-3-Pyr | Bnzl-4-F |
| 108 | Z$^4$ = CCH$_2$NMe$_2$ all others = CH | O-Bnzl | NH-3-Pyr | Bnzl-4-F |
| 109 | Z$^4$ = CC(O)NMe$_2$ all others = CH | O-Bnzl | NH-3-Pyr | BnzL-4-F |
| 110 | Z$^4$ =CBr all others = CH | O-Bnzl | NH-3-Pyr | Bnzl-4-F |
| 111 | Z$^4$ = CSO$_2$NH$_2$ all others = CH | O-Bnzl | NH-3-Pyr | Bnzl-4-F |
| 112 | Z$^3$ = CC(Me)$_2$OH all others = CH | OCH$_2$-4-Pyr | NH-4-Pyr | Bnzl-4-CF$_3$ |
| 113 | Z$^3$ = CCO$_2$H all others = CH | OCH$_2$-4-Pyr | NH-4-Pyr | Bnzl-4-CF$_3$ |

-continued

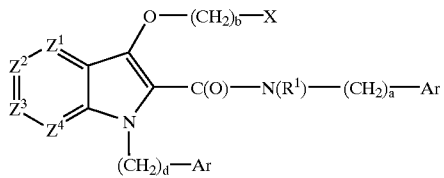

I

| Cpd | Z's | —(O)—(CH$_2$)$_b$—X | N(R$^1$)(CH$_2$)$_a$—Ar | (CH$_2$)$_d$-Ar |
|---|---|---|---|---|
| 114 | Z$^3$ = CCH$_2$NMe$_2$ all others = CH | OCH$_2$-4-Pyr | NH-4-Pyr | Bnzl-4-CF$_3$ |
| 115 | Z$^3$ = CC(O)NMe$_2$ all others = CH | OCH$_2$-4-Pyr | NH-4-Pyr | Bnzl-4-CF$_3$ |
| 116 | Z$^3$ =CBr all others = CH | OCH$_2$-4-Pyr | NH-4-Pyr | Bnzl-4-CF$_3$ |
| 117 | Z$^3$ = CSO$_2$NH$_2$ all others = CH | OCH$_2$-4-Pyr | NH-4-Pyr | Bnzl-4-CF$_3$ |
| 118 | Z$^3$ = CC(Me)$_2$OH all others = CH | O-Bnzl | NH-3-Pyr | Bnzl-4-F |
| 119 | Z$^3$ = CCO$_2$H all others = CH | O-Bnzl | NH-3-Pyr | Bnzl-4-F |
| 120 | Z$^3$ = CCH$_2$NMe$_2$ all others = CH | O-Bnzl | NH-3-Pyr | Bnzl-4-F |
| 121 | Z$^3$ = CC(O)NMe$_2$ all others = CH | O-Bnzl | NH-3-Pyr | Bnzl-4-F |
| 122 | Z$^3$ =CBr all others = CH | O-Bnzl | NH-3-Pyr | Bnzl-4-F |
| 123 | Z$^3$ = CSO$_2$NH$_2$ all others = CH | O-Bnzl | NH-3-Pyr | Bnzl-4-F |
| 124 | Z$^2$ = CC(Me)$_2$OH all others = CH | OCH$_2$-4-Pyr | NH-4-Pyr | Bnzl-4-CF$_3$ |
| 125 | Z$^2$ = CCO$_2$H all others = CH | OCH$_2$-4-Pyr | NH-4-Pyr | Bnzl-4-CF$_3$ |
| 126 | Z$^2$ = CCH$_2$NMe$_2$ all others = CH | OCH$_2$-4-Pyr | NR-4-Pyr | Bnzl-4-CF$_3$ |
| 127 | Z$^2$ = CC(O)NMe$_2$ all others = CH | OCH$_2$-4-Pyr | NH-4-Pyr | Bnzl-4-CF$_3$ |
| 128 | Z$^2$ =CBr all others = CH | OCH$_2$-4-Pyr | NH-4-Pyr | Bnzl-4-CF$_3$ |
| 129 | Z$^2$ = CSO$_2$NH$_2$ all others = CH | OCH$_2$-4-Pyr | NH-4-Pyr | Bnzl-4-CF$_3$ |
| 130 | Z$^2$ = CC(Me)$_2$OH all others = CH | O-Bnzl | NR-3-Pyr | Bnzl-4-F |
| 131 | Z$^2$ = CCO$_2$H all others = CH | O-Bnzl | NH-3-Pyr | Bnzl-4-F |
| 132 | Z$^2$ = CCH$_2$NMe$_2$ all others = CH | O-Bnzl | NH-3-Pyr | Bnzl-4-F |
| 133 | Z$^2$ = CC(O)NMe$_2$ all others = CH | O-Bnzl | NH-3-Pyr | Bnzl-4-F |
| 134 | Z$^2$ =CBr all others = CH | O-Bnzl | NH-3-Pyr | Bnzl-4-F |
| 135 | Z$^2$ = CSO$_2$NH$_2$ all others = CH | O-Bnzl | NH-3-Pyr | Bnzl-4-F |
| 136 | CH | O-Bnzl | NH-3-Pyr | Bnzl-4-C(Me)$_2$—OH |
| 137 | CH | OCH$_2$-3-Pyr | NH-3-Pyr | Bnzl-4-F |
| 138 | CH | OCH$_2$-3-Pyr | NH-4-Pyr | Bnzl-4-F |

-continued $$\text{I}$$

Structure I: pyrrole with Z¹,Z²,Z³,Z⁴ fused ring, O—(CH₂)ᵦ—X at 3-position, C(O)—N(R¹)—(CH₂)ₐ—Ar at 2-position, N—(CH₂)ₐ—Ar

| Cpd | Z's | —(O)—(CH₂)ᵦ—X | N(R¹)(CH₂)ₐ—Ar | (CH₂)ₐ-Ar |
|---|---|---|---|---|
| 139 | CH | OCH₂-3-Pyr | NH-Phe-3,4-di-OMe | Bnzl-4-F |
| 140 | CH | OCH₂-3-Pyr | NH-Phe-3,4-di-F | Bnzl-4-F |
| 141 | CH | OCH₂-3-Pyr | NH-5-Pyr-2-OMe | Bnzl-4-F |
| 142 | CH | O-Bnzl | NH-3-Pyr | Bnzl-4-CO₂Me |
| 143 | CH | OCH₂-3-Pyr | NH-5-tetrazolyl | Bnzl-4-F |
| 144 | CH | OCH₂-3-Pyr | NH-4-Pyr-2-OMe | Bnzl-4-F |
| 145 | CH | OCH₂-3-Pyr | NH-5-Pyr-2-CN | Bnzl-4-F |
| 146 | CH | OCH₂-3-Pyr | NH-5-Pyr-2-NHC(O)Me | Bnzl-4-F |
| 147 | CH | O-Bnzl | NH-Phe-3-SO₂Me | Bnzl-4-F |
| 148 | CH | O-Bnzl | NH-3-Pyr | Bnzl-4-CF₃ |
| 149 | CH | O-CH₂-cPr | NH-Phe-3,4-di-OMe | Bnzl-4-t-Bu |
| 150 | CH | O-CH₂-cPr | NH-5-tetrazolyl | Bnzl-4-t-Bu |
| 151 | CH | O-CH₂-cPr | NH-4-Pyr-2-OMe | Bnzl-4-t-Bu |
| 152 | CH | O-CH₂-cPr | NH-5-Pyr-2-OMe | Bnzl-4-t-Bu |
| 153 | CH | O-CH₂-cPr | NH-4-Pyr-2-NHC(O)OEt | Bnzl-4-t-Bu |
| 154 | CH | O-CH₂-cPr | NH-3-Pyr | Bnzl-4-F |
| 155 | CH | O-CH₂-cPr | NH-4-Pyr | Bnzl-4-F |
| 156 | CH | O-CH₂-cPr | NH-Phe-3,4-di-OMe | Bnzl-4-F |
| 157 | CH | O-CH₂-cPr | NH-Phe-3,4-di-F | Bnzl-4-F |
| 158 | CH | O-CH₂-cPr | NH-5-Pyr-2-OMe | Bnzl-4-F |
| 159 | CH | O-CH₂-cPr | NH-5-tetrazolyl | Bnzl-4-F |
| 160 | CH | O-CH₂-cPr | NH-4-Pyr-2-OMe | Bnzl-4-F |
| 161 | CH | O-CH₂-cPr | NH-5-Pyr-2-NHC(O)Me | Bnzl-4-F |
| 162 | CH | OCH₂-4-Pyr | NH-3-Pyr | Bnzl-4-F |
| 163 | CH | OCH₂-4-Pyr | NH-4-Pyr | Bnzl-4-F |
| 164 | CH | OCH₂-4-Pyr | NH-Phe-3,4-di-OMe | Bnzl-4-F |
| 165 | CH | OCH₂-4-Pyr | NH-Phe-3,4-di-F | Bnzl-4-F |
| 166 | CH | OCH₂-4-Pyr | NH-5-Pyr-2-OMe | Bnzl-4-F |
| 167 | CH | OCH₂-4-Pyr | NH-5-tetrazolyl | Bnzl-4-F |
| 168 | CH | OCH₂-4-Pyr | NH-4-Pyr-2-OMe | Bnzl-4-F |
| 169 | CH | OCH₂-4-Pyr | NH-5-Pyr-2-CN | Bnzl-4-F |
| 170 | CH | OCH₂-4-Pyr | NH-5-Pyr-2-NHC(O)Me | Bnzl-4-F |
| 171 | CH | OCH₂-4-Pyr | NH-4-Pyr-2-NHC(O)OEt | Bnzl-4-F |
| 172 | CH | O-Bnzl | NM-3-Pyr | Bnzl-4-t-Bu |
| 173 | CH | O-Bnzl | NH-3-Pyr | Bnzl-4-F |
| 174 | CH | O-Bnzl | NH-4-Pyr | Bnzl-4-F |
| 175 | CH | O-Bnzl | NH-Phe-3,4-di-OMe | Bnzl-4-F |
| 176 | CH | O-Bnzl | NH-Phe-3,4-di-F | Bnzl-4-F |
| 177 | CH | O-Bnzl | NH-5-Pyr-2-OMe | Bnzl-4-F |
| 178 | CH | O-Bnzl | NH-5-tetrazolyl | Bnzl-4-F |
| 179 | CH | O-Bnzl | NH-4-Pyr-2-OMe | Bnzl-4-F |
| 180 | CH | O-Bnzl | NH-5-Pyr-2-CN | Bnzl-4-F |
| 181 | CH | O-Bnzl | NH-5-Pyr-2-NHC(O)Me | Bnzl-4-F |
| 182 | CH | O-Bnzl | NH-4-Pyr-2-NHC(O)OEt | Bnzl-4-F |
| 183 | CH | O-Bnzl | N(Me)-3-Pyr | Bnzl-4-F |
| 184 | CH | O-Bnzl | N(Me)-3-Pyr | Bnzl-4-CF₃ |

-continued

![Structure I]

| Cpd | Z's | —(O)—(CH₂)ᵦ—X | N(R¹)(CH₂)ₐ—Ar | (CH₂)ᵈ-Ar |
|---|---|---|---|---|
| 185 | CH | O-Bnzl | 3-pyridylmethyl | Bnzl-4-F |
| 186 | CH | O-Bnzl | 4-pyridylmethyl | Bnzl-4-F |

Phe = phenyl, Bzyl = benzyl, Pyr = pyridyl or a pharmaceutically acceptable salt or hydrate thereof.

13. A compound selected from the group consisting of:

{1-[(4-Fluorophenyl)methyl]-3-(phenylmethoxy)indol-2-yl}-N-(3-pyridyl)formamide;

{1-[(4-Fluorophenyl)methyl]-3-(phenylmethoxy)indol-2-yl}-N-[3-(methylsulfonyl) phenyl]formamide;

{1-[(4-Fluorophenyl)methyl]-3-(phenylmethoxy)indol-2-yl}-N-(3-pyridylmethyl)formamide;

{1-[(4-Fluorophenyl)methyl]-3-(phenylmethoxy)indol-2-yl}-N-(4-pyridylmethyl)formamide;

(1-{[4-(1-Hydroxyisopropyl)phenyl]methyl}-3-(phenylmethoxy)indol-2-yl}-N-(3-pyridyl)formamide;

{1-[(4-Methylphenyl)methyl]-3-(phenylmethoxy)indol-2-yl}-N-(3-pyridyl)formamide;

(1-{[4-(tert-Butyl)phenyl]methyl}-3-(phenylmethoxy)indol-2-yl}-N-(3-pyridyl)formamide;

(1-{[4-(Trifluoromethyl)phenyl]methyl}-3-(phenylmethoxy)indol-2-yl)-N-(3-pyridyl)formamide;

(1-{[4-(Difluoromethoxy)phenyl]methyl}-3-(phenylmethoxy)indol-2-yl)-N-(3-pyridyl)formamide;

{3-(Cyclopropylmethoxy)-1-[(4-fluorophenyl)methyl] indol-2-yl}-N-(3-pyridyl)formamide;

{1-[(4-Fluorophenyl)methyl]-3-(4-pyridylmethoxy) indol-2-yl}-N-(3-pyridyl)formamide;

{1-[(4-Fluorophenyl)methyl]-3-[(3-methoxyphenyl) methoxy]indol-2-yl}-N-(3-pyridyl)formamide;

{5-Bromo-1-[(4-fluorophenyl)methyl]-3-(phenylmethoxy)indol-2-yl}-N-(3-pyridyl)formamide;

{1-[(4-Fluorophenyl)methyl]-5-(1-hydroxy-isopropyl)-3-(phenylmethoxy)indol-2-yl}-N-(3-pyridyl)formamide;

1-[(4-Fluorophenyl)methyl]-3-(phenylmethoxy)-2-(N-(3-pyridyl)carbamoyl)indole-5-carboxylic acid;

{1-[(4-Fluorophenyl)methyl]-4-(1-hydroxy-isopropyl)-3-(phenylmethoxy)indol-2-yl}-N-(3-pyridyl)formamide; and {1-[(4-Fluorophenyl)methyl]-6-(1-hydroxy-isopropyl)-3-(phenylmethoxy)indol-2-yl}-N-(3-pyridyl)formamide, or a pharmaceutically acceptable salt or hydrate thereof.

14. A pharmaceutical composition comprised of a compound in accordance with claim 1 in combination with a pharmaceutically acceptable carrier.

15. A method of treating or preventing a PDE-IV mediated disease or condition in a mammalian patient in need thereof, comprising administering to said patient a compound represented by formula I:

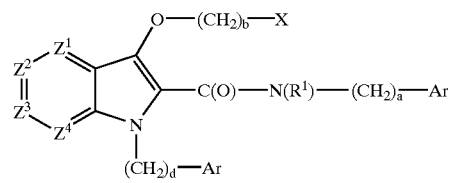

or a pharmaceutically acceptable salt or hydrate thereof wherein:

one of $Z^1$, $Z^2$, $Z^3$ and $Z^4$ represents N or $CR^2$ and the others represent $CR^2$;

a represents 0 or 1;

b represents 0, 1 or 2;

d represents 0, 1 or 2;

$R^1$ represents H, $C_{1-4}$alkyl or hydroxy$C_{1-4}$alkyl;

each $R^2$ is independently selected from the group consisting of:

H, halo, $C_{1-8}$alkyl, halo$C_{1-8}$alkyl, hydroxy$C_{1-8}$alkyl, CN, Het, $OR^a$, $OC(O)N(R^b)_2$, $NR^bC(O)R^a$, $C(R^a)_2CO_2R^a$, $C_{1-8}$alkyl$N(R^b)_2$, halo$C_{1-8}$alkyl$N(R^b)_2$, $CO_2R^a$, $C(O)N(R^b)_2$, $SO_{2N(R^b)_2}$, $S(O)_bR^d$ and $NR^bSO_2R^d$;

each $R^a$ is independently selected from H, $C_{1-4}$alkyl, $C_{1-4}$alkylNH$C_{1-4}$alkyl, and $C_{1-4}$alkylN($C_{1-4}$alkyl)$_2$, the alkyl portions of which are optionally substituted with 1–3 halo groups;

each $R^b$ is selected from H and $C_{1-7}$alkyl, and when two $R^b$'s are present, they can be taken together and represent a fused ring system having 5–10 members, said ring system being saturated or containing 1–4 double bonds, and optionally including 1–3 heteroatoms selected from O, S and $NR^e$;

$R^d$ and $R^e$ are independently selected from Het, $C_{1-7}$alkyl, $C_{2-7}$alkenyl, $C_{2-7}$alkynyl, and $C_{1-7}$alkyl-Het;

Het represents a 5–10 membered aromatic, partially aromatic or non-aromatic ring system containing 1–4 heteroatoms selected from O, S and N, optionally substituted on any available position with oxo, $C_{1-4}$alkyl, halo, amino, hydroxy$C_{1-4}$ alkyl, halo$C_{1-4}$alkyl and amino$C_{1-4}$alkyl;

X represents $C_{3-7}$cycloalkyl or Ar;

and each Ar is independently selected from the group consisting of: phenyl, thienyl, thiazolyl, pyridyl, oxazolyl, tetrazolyl, pyrimidinyl, pyrazinyl and pyridazinyl, said Ar being optionally substituted with 1–4 members selected from: halo, hydroxy, CN, $C_{1-4}$alkyl, $C_{1-6}$haloalkyl, $C_{1-6}$hydroxyalkyl, $OC_{1-6}$alkyl, $OC_{1-6}$haloalkyl, $OC_{1-6}$hydroxyalkyl, $C_{1-6}$alkyl$OC_{1-6}$alkyl, $C_{1-6}$alkyl$OC_{1-6}$haloalkyl, $C(O)NH_2$, $C(O)NHC_{1-6}$alkyl, $C(O)N(C_{1-6}$alkyl$)_2$, $C_{1-6}$alkyl$OC_{1-6}$alkyl$C(O)NH_2$, $CO_2H$, $CO_2C_{1-6}$alkyl, $NHC(O)C_{1-6}$alkyl, $NHC(O)OC_{1-6}$alkyl, and $SO_2C_{1-6}$alkyl, in an amount that is effective for treating or preventing said PDE-IV mediated disease or condition.

16. A method in accordance with claim 15 wherein the disease or condition is selected from the group consisting of:

inflammatory response or muscular spasm; bladder or alimentary smooth muscle spasm; asthma; inflamed lung associated with asthma; cystic fibrosis; chronic bronchitis; eosinophilic granuloma; psoriasis; other benign and malignant proliferative skin diseases; endotoxic shock; septic shock; ulcerative colitis; Crohn's disease; reperfusion injury of the myocardium or brain; inflammatory arthritis; osteoporosis, chronic glomerulonephritis; atopic dermatitis; urticaria; adult or infant respiratory distress syndrome; diabetes; diabetes insipidus; allergic rhinitis; allergic conjunctivitis; vernal conjunctivitis; arterial restenosis and atherosclerosis.

17. A method in accordance with claim 15 wherein the disease or condition is selected from the group consisting of: pain; cough; fever; rheumatoid arthritis; osteoarthritis; ankylosing spondylitis; transplant rejection; graft versus host disease; hypersecretion of gastric acid; bacterial, fungal or viral induced infection or sepsis; septic shock; cachexia and muscle wasting; depression; memory impairment; and prevention of tumor growth and invasion of normal tissues.

* * * * *